(12) United States Patent
Pravda

(10) Patent No.: US 7,312,243 B1
(45) Date of Patent: *Dec. 25, 2007

(54) MATERIALS AND METHODS FOR TREATMENT OF GASTROINTESTINAL DISORDERS

(76) Inventor: Jay Pravda, P.O. Box 142181, Gainesville, FL (US) 32614-2181

( * ) Notice: Subject to any disclaimer, the term of this patent is extended or adjusted under 35 U.S.C. 154(b) by 68 days.

This patent is subject to a terminal disclaimer.

(21) Appl. No.: 10/927,742

(22) Filed: Aug. 27, 2004

Related U.S. Application Data

(60) Provisional application No. 60/499,152, filed on Aug. 29, 2003.

(51) Int. Cl.
| | |
|---|---|
| A61K 31/355 | (2006.01) |
| A61K 31/12 | (2006.01) |
| A61K 31/522 | (2006.01) |
| A61K 31/35 | (2006.01) |
| A61K 33/24 | (2006.01) |
| A61K 33/04 | (2006.01) |
| A01N 43/16 | (2006.01) |
| A01N 35/00 | (2006.01) |
| A01N 43/90 | (2006.01) |
| A01N 59/16 | (2006.01) |
| A01N 59/02 | (2006.01) |

(52) U.S. Cl. ............... 514/458; 514/263.34; 514/456; 514/689; 424/653; 424/709; 424/711

(58) Field of Classification Search ............... 424/435, 424/436, 641, 709, 711, 719
See application file for complete search history.

(56) References Cited

U.S. PATENT DOCUMENTS 5,563,131 A * 10/1996 Berliner et al. ............. 514/177
5,817,630 A * 10/1998 Hofmann et al. ............. 514/18

OTHER PUBLICATIONS

Babior BM et al. Journal of Biological Chemistry 1981, 265(5), 2321-2323.*
STN accession No. 94:19076 Kondracki Dissertation Abstracts International 1993, 54(12B) p. 6208.*
Edwin van den Worm Investigation on apocynin a potent NADPH oxidase inhibitor publication date: May 2001. title page and p. 75.*
Pfaff et al. Chromotographia 1999, 48(11/12), 666-670.*
Doussiere et al. Eur. J. Biochem. 1992, 208, 61-71.*
Abraham, N. et al. "Is smoking an indirect risk factor for the development of ulcerative colitis? An age- and sex-matched case-control study" *Journal of Gastroenterology and Hepatology*, 2003, pp. 139-146, vol. 18.
Allison, M. C. et al. "Prevalence of proximal faecal stasis in active ulcerative colitis" *Gut*, 1991, pp. 179-182, vol. 32.
Aw, T. Y. "Molecular and cellular responses to oxidative stress and changes in oxidation-reduction imbalance in the intestine" *Am. J. Clin. Nutr.*, 1999, pp. 557-565, vol. 70.
Bagchi, D. et al. "Stress, Diet and Alcohol-induced Oxidative Gastrointestinal Mucosal Injury in Rats and Protection by Bismuth Subsalicylate" *J. Appl. Toxicol*, 1998, pp. 3-13, vol. 18, No. 1.
Basit, A. et al. "Perspectives on Colonic Drug Delivery" *Pharmatech*, 2003, pp. 185-190.
Batist, G. et al. "Interindividual variation in phase II detoxification enzymes in normal human colon mucosa" *Biochemical Pharmacology*, 1988, pp. 4241-4243, vol. 37, No. 21.
Beaugerie, L. et al. "Impact of Cessation of Smoking on the Course of Ulcerative Colitis" *The American Journal of Gastroenterology*, 2001, pp. 2113-2116, vol. 96, No. 7.
Benson, K. W. et al. "Fecal Impaction" *Am. J. Sc.*, 1939, pp. 541-545, vol. 198.
Bertz, R. J. et al. "Use of In Vitro and In Vivo Data to Estimate the Likelihood of Metabolic Pharmacokinetic Interactions" Mar. 1997, pp. 210-258, vol. 32, No. 3.
Beutler, E. et al. "Ethnic Variation in Red Cell Glutathione Peroxidase Activity" *Blood*, Jul. 1975, pp. 103-110, vol. 46, No. 1.
Black, D. A. et al. "Transit Time in Ulcerative Proctitis" *Scand. J. Gastroenterol*, 1987, pp. 872-876, vol. 22.
Blau, S. et al. "Differences in the reducing power along the rat GI tract: Lower antioxidant capacity of the colon" *Molecular and Cellular Biochemistry*, 1999, pp. 185-191, vol. 194.
Boveris, A. et al. "The Mitochondrial Generation of Hydrogen Peroxide" *Biochem. J.*, 1973, pp. 707-716, vol. 134.
Boveris, A. et al. "The Cellular Production of Hydrogen Peroxide" *Biochem. J.*, 1972, pp. 617-630, vol. 128.
Boveris, A. et al. "Mitochondrial Production of Hydrogen Peroxide Regulation by Nitric Oxide and the Role of Ubisemiquinone" *Life*, 2000, pp. 245-250, vol. 50.
Brunner, L. S. "Perioperative Management of the Surgical Patient" In *Textbook of Medical Surgical Nursing*, 4th edition, 1980, p. 358, Lippincott, Philadelphia.

(Continued)

Primary Examiner—Johann Richter
Assistant Examiner—Ernst V Arnold
(74) Attorney, Agent, or Firm—Saliwanchik, Lloyd & Saliwanchik

(57) ABSTRACT

The subject invention pertains to materials and methods for the prevention and treatment of gastrointestinal diseases, including inflammatory bowel diseases such as Crohn's disease and ulcerative colitis. Therapeutic compositions of the invention include compositions that can neutralize hydrogen peroxide, such as reducing agents and oxidizing agents. In one embodiment, a therapeutic composition of the invention comprises a reducing agent such as sodium thiosulfate. Therapeutic compositions of the invention can optionally include compounds with antibacterial activity, compositions that inhibit bacterial adherence to cells and tissue, compositions that inhibits epithelial lipid peroxidation, compositions that add viscosity to a solution, compositions that inhibit most cells, and/or compositions that help to seal or repair tight junctions between cells of the colonic epithelium of the gastrointestinal tract. Methods of the invention include administration of compounds or compositions of the invention. In one embodiment, compounds or compositions of the invention are rectally instilled in a patient.

8 Claims, No Drawings

OTHER PUBLICATIONS

Cadenas, E. et al. "Mitochondrial Free Radical Generation, Oxidative Stress, and Aging" *Free Radical Biology & Medicine*, 2000, pp. 222-230, vol. 29, Nos. 3-4.

Caprari, P. et al. "6-Phosphogluconate dehydrogenase deficiency in an Italian family" *Ann. Hematol.*, 2001, pp. 41-44, vol. 80.

Carpenter, H. A. et al. "The Importance of Clinicopathological Correlation in the Diagnosis of Inflammatory Conditions of the Colon: Histological Patterns With Clinical Implications" *The American Journal of Gastroenterology*, 2000, pp. 878-896, vol. 95, No. 4.

Chance, B. et al. "Hydroperoxide Metabolism in Mammalian Organs" *Physiological Reviews*, Jul. 1979, pp. 527-605, vol. 59, No. 3.

Chen, N. et al. "Physiologic concentrations of homocysteine inhibit the human plasma GSH peroxidase that reduces organic hydroperoxides" *J. Lab. Clin. Med.*, 2000, pp. 58-65, vol. 136, No. 1.

Chen, S. et al. "Hydroxyl-radical production in physiological reactions" *Eur. J. Biochem.*, 1999, pp. 726-735, vol. 260.

Cho, J. H. et al. "Identification of novel susceptibility loci for inflammatory bowel disease on chromosomes 1p, 3q, 4q: Evidence for epistasis between 1p and IBD1" *Proc. Natl. Acad. Sci. USA*, Jun. 1998, pp. 7502-7507, vol. 95.

Cho, J. H. et al. "Linkage and linkage disequillibrium in chromosome band 1p36 in American Chaldeans with inflammatory bowel disease" *Human Molecular Genetics*, 2000, pp. 1425-1432, vol. 9, No. 9.

Ciftci, M. et al. "Effects of Some Drugs on Rat Erythrocyte 6-Phosphogluconate Dehydrogenase: An In Vitro and In Vivo Study" *Polish Journal of Pharmacology*, 2002, pp. 275-280, vol. 54.

Dalekos G. N. et al. "Zinc, copper and immunological markers in the circulation of well nourished patients with ulcerative colitis" *Eur. J. Gastroenterol Hepatol.*, Apr. 1998, pp. 331-337, vol. 10, No. 4, abstract only.

Davidson, R. G. "Electrophoretic variants of human 6-phosphogluconate dehydrogenase: population and family studies and description of a new variant" *Ann. Hum. Genet.*, 1967, pp. 355-361, vol. 30.

Davies, K. J. A. "Oxidative Stress, Antioxidant Defenses, and Damage Removal, Repair, and Replacement Systems" *Life*, 2000, pp. 279-289, vol. 50.

Dern, R. J. et al. "Hereditary variation of erythrocytic 6-phosphogluconate dehydrogenase" *J. Lab. & Clin. Med.*, Feb. 1966, pp. 255-264, vol. 67, No. 2.

Drossman, D. et al. "Rome II: the functional gastrointestinal disorders : diagnosis, pathophysiology, and treatment : a multinational consensus" in *The Functional Gastrointestinal Disorders*, 2000, eds. Douglas A. Dross, Enrico Corazziari, Library of Congress Catloging-in-Publication Data.

Drossman, D. A. et al. "U.S. Householder Survey of Functional Gastrointestinal Disorders" *Digestive Diseases and Sciences*, Sep. 1993, pp. 1569-1580, vol. 38, No. 9.

Duncan, G. G. "Folic Acid (Folacin)" In *Diseases of Metabolism—Detailed Methods of Diagnosis and Treatment*, 5th edition, 1964, pp. 614-618, W. B. Saunders Company, Philadelphia and London.

Eaton, J. W. et al. "Acatalasemia" In *The Metabolic & Molecular Bases of Inherited Disease*, 7th edition, Chapter 74, eds., Scriver et al., 1995, pp. 2371-2379, McGraw-Hill Medical Publishing Division.

Eaton, J. W. et al. "Molecular Bases of Cellular Iron Toxicity" *Free Radical Biology & Medicine*, 2002, pp. 833-840, vol. 32, No. 2.

Eberhardt, M. K. et al., In *Reactive Oxygen Metabolites—Chemistry and Medical Consequences*, 2001, pp. 23, 51, 63, 64, 81, 118, 125, and 262, CRC Press.

Elsborg, L. et al. "Folate Deficiency in Chronic Inflammatory Bowel Diseases" *Scand. J. Gastroent.*, 1979, pp. 1019-1023, vol. 14.

Everhart, J. E. et al. "A Longitudinal Survey of Self-Reported Bowel Habits in the United States" *Digestive Diseases and Sciences*, Aug. 1989, pp. 1153-1162, vol. 34, No. 8.

Everson, C. A. et al. "Systemic bacterial invasion induced by sleep deprivation" *Am. J. Physiol. Regulatory Integrative Comp. Physiol.*, 2000, pp. R905-R916, vol. 278.

Farrell, R. J. et al. "Ulcerative colitis" *The Lancet*, Jan. 26, 2002, pp. 331-340, vol. 359.

Farrokhar, F. et al. "A Critical Review of Epidemiological Studies in Inflammatory Bowel Disease" *Scand. J. Gastroenterol.*, 2001, pp. 2-15, vol. 36, No. 1.

Fernandez-Banares, F. et al. "Vitamin Status In Patients with Inflammatory Bowel Disease" *The American Journal of Gastroenterology*, 1989, pp. 744-748, vol. 84, No. 7.

Fowler, J. S. et al. "Monoamine Oxidase and Cigarette Smoking" *NeuroToxicology*, 2003, pp. 75-82, vol. 24.

Fridovich, I. "Oxygen Toxicity: A Radical Explanation" *The Journal of Experimental Biology*, 1998, pp. 1203-1209, vol. 201.

Friedman, G. et al. "A Common Mutation A1298C in Human Methylenetetrahydrofolate Reductase Gene: Association with Plasma Gene: Association with Plasma Total Homocysteine and Folate Concentrations" *J. Nutr.*, 1999, pp. 1656-1661, vol. 129.

Geerling, B. J. et al. "Diet as a Risk Factor for the Development of Ulcerative Colitis" *The American Journal of Gastroenterology*, 2000, pp. 1008-1013, vol. 95, No. 4.

Goglia, F. et al. "Thyroid Hormones and Mitochondria" *Bioscience Reports*, Feb. 2002, pp. 17-29, vol. 22, No. 1.

Gordillo, E. et al. "Implication of Lysine Residues in the Loss of 6-Phosphogluconate Dehydrogenase Activity in Aging Human Erythrocytes" *Mechanisms of Ageing and Development*, 1991, pp. 291-297, vol. 59.

Goyette, P. et al. "Gene structure of human and mouse methylenetetrahydrofolate reductase (MTHFR)" *Mammalian Genome*, 1998, pp. 652-656, vol. 9.

Graf, E. et al. "Iron-catalyzed Hydroxyl Radical Formation" *The Journal of Biological Chemistry*, Mar. 25, 1984, pp. 3620-3624, vol. 259, No. 6.

Granger, D. N. et al. "Role of Oxygen Radicals in the Pathogenesis of Intestinal Ischemia" *The Physiologist*, 1983, pp. 159-164, vol. 26, No. 3.

Grisham, M. B. et al. "Oxidant Defense Mechanisms in the Human Colon" *Inflammation*, 1990, pp. 669-680, vol. 14, No. 6.

Gulati, S. et al. "Alterations of peroxisomal function in ischemia-reperfusion injury of rat kidney" *Biochimica et Biophysica Acta*, 1993, pp. 291-298, vol. 1182, No. 3.

Guyton, A. C. et al. "Functional Organization of the Human Body and Control of the 'Internal Environment'" In *Human Physiology and Mechanisms of Disease*, 1997, Chapter 1, 6th edition, p. 3, W. B. Saunders Company.

Han, D. et al. "Mitochondrial respiratory chain-dependent generation of superoxide anion and its release into the intermembrane space" *Biochem. J.*, 2001, pp. 411-416, vol. 353.

Harris, M. L. et al. "Free Radicals and Other Reactive Oxygen Metabolites in Inflammatory Bowel Disease: Cause, Consequence or Epiphenomenon?" *Pharmac. Ther.*, 1992, pp. 375-408, vol. 53.

Hendrickson, B. A. et al. "Clinical Aspects and Pathophysiology of Inflammatory Bowel Disease" *Clinical Microbiology Reviews*, Jan. 2002, pp. 79-94, vol. 15, No. 1.

Hoek, J. B. et al. "Alcohol and Mitochondria: A Dysfunctional Relationship" *Gastroenterology*, 2002, pp. 2049-2063, vol. 122.

Huycke, M. M. et al. "Extracellular superoxide production by *Enterococcus faecalis* requires demethylmenaquinone and is attenuated by functional terminal quinol oxidases" *Molecular Microbiology*, 2001, pp. 729-740, vol. 42, No. 3.

Huycke, M. M. et al. "*Enterococcus faecalis* produces extracellular superoxide and hydrogen peroxide that damages colonic epithelial cell DNA" *Carcinogenesis*, 2002, pp. 529-536, vol. 23, No. 3.

Isman, C. A. et al. "Methimazole-induced hypothyroidism in rats ameliorates oxidative injury in experimental colitis" *Journal of Endocrinology*, 2003, pp. 471-476, vol. 177.

Jarnerot, G. et al. "The Thyroid in Ulcerative Colitis and Crohn's Disease" *Acta Med. Scand.*, 1975, pp. 83-87, vol. 197.

Karlinger, K. et al. "The epidemiology and the pathogenesis of inflammatory bowel disease" *Eur. J. Radiol.*, Sep. 2000, pp. 154-167, vol. 35, No. 3, abstract only.

Keyer, K. et al. "Superoxide accelerates DNA damage by elevating free-iron levels" *Proc. Natl. Acad. Sci. USA*, Nov. 1996, pp. 13635-13640, vol. 93.

Koutroubakis, I. E. et al. "Hyperhomocysteinemia in Greek Patients with Inflammatory Bowel Disease" *Digestive Diseases and Sciences*, Dec. 2000, pp. 2347-2351, vol. 45, No. 12.

Kowaltowski, A. J. et al. "Reactive Oxygen Generation by Mitochondria" In *Mitochondria in Pathogenesis*, 2001, Chapter 14, eds. J. J. Lemasters et al., pp. 281-286, Kluwer Academic/Plenum Publishers.

Larsson, A. et al. "Glutathione Synthetase Deficiency and Other Disorders of the γ-Glutamyl Cycle" In *The Metabolic & Molecular Bases of Inherited Disease*, 8th edition, Chapter 96, ed. Scriver et al., 2001, pp. 2205-2215, McGraw-Hill Medical Publishing Division.

Lechin, F. et al. "Stress Versus Depression" *Prog. Neuro-Psychopharmacol. & Biol. Psychiat.*, 1996, pp. 899-902, 930, 933, and 932, vol. 20.

Li, C. et al. "Reactive species mechanisms of cellular hypoxia-reoxygenation injury" *Am. J. Physiol. Cell Physiol.*, 2002, pp. C227-C241, vol. 282.

Liochev, S. I. et al. "Superoxide and Iron: Partners in Crime" *Life*, 1999, pp. 157-161, vol. 48.

Liu, S. "Generating, Partitioning, Targeting and Functioning of Superoxide in Mitochondria" *Bioscience Reports*, 1997, pp. 259-272, vol. 17, No. 3.

Mahmud, N. et al. "Increased prevalence of methylenetetrahydrofolate reductase C677T variant in patients with inflammatory bowel disease and its clinical implications" *Gut*, 1999, pp. 389-394, vol. 45.

Madretsma, S. et al. "In-vivo effect of nicotine on cytokine production by human non-adherent mononuclear cells" *Eur. J. Gastroenterol. Hepatol.*, Oct. 1996, pp. 1017-1020, vol. 8, No. 10, abstract only.

Maier, B. R. et al. "Effects of a high-beef diet on bowel flora: a preliminary report" *The American Journal of Clinical Nutrition*, Dec. 1974, pp. 1470-1474, vol. 27.

Meyer, C. T. et al. "Hydrogen Peroxide Colitis: A Report of Three Patients" *J. Clin. Gastroenterol.*, 1981, pp. 31-35, vol. 3.

Meyers, S. et al. "The "Natural History" of Ulcerative Colitis: An Analysis of the Placebo Response" *J. Clin. Gastroenterol.*, 1989, pp. 33-37, vol. 11, No. 1.

Millar, A. D. et al. "Effects of Iron and iron chelation in vitro on mucosal oxidant activity in ulcerative colitis" *Aliment Parmacol. Ther.*, 2000, pp. 1163-1168, vol. 14.

Modebe, O. "Autoimmune thyroid disease with ulcerative colitis" *Postgraduate Medical Journal*, 1986, pp. 475-476, vol. 62.

Nelson, M. S. "Biochemical and Genetic Characterization of the Lowell Variant. A New Phenotype of 6-Phosphogluconate Dehydrogenase" *Human Genetics*, 1982, pp. 333-336, vol. 62.

Odes, H. S. et al. "Effects of Current Cigarette Smoking on Clinical Course of Crohn's Disease and Ulcerative Colitis" *Digestive Diseases and Sciences*, Aug. 2001, pp. 1717-1721, vol. 46, No. 8.

O'Donnell, V. B. et al. "High rates of extracellular superoxide generation by cultured human fibroblasts: Involvement of a lipid-metabolizing enzyme" *Biochem. J.*, 1996, pp. 805-812, vol. 318.

Oren, R. et al. "Anti-thyroid drugs decrease mucosal damage in a rat model of experimental colitis" *Aliment Pharmacol. Ther.*, 1997, pp. 341-345, vol. 11.

Outinen, P. A. et al. "Homocysteine-Induced Endoplasmic Reticulum Stress and Growth Arrest Leads to Specific Changes in Gene Expression in Human Vascular Endothelial Cells" *Blood*, Aug. 1, 1999, pp. 959-967, vol. 94, No. 3.

Ouyang, Y. et al. "Suppression of human IL-1β, IL-2, IFN-γ and TNF-α production by cigarette smoke extracts" *J. Allergy Clin. Immunology*, 2000, pp. 280-287, vol. 106, No. 2.

Owen, R. W. et al. "Generation of reactive oxygen species by the faecal matrix" *Gut*, 2000, pp. 225-232, vol. 46.

Parks, D. A. et al. "Oxygen radicals: effects on intestinal vascular permeability" *Gastrointest. Liver Physiol.*, 1984, pp. G167-G170, vol. 10.

Parks, D. A. et al. "Contributions of ischemia and reperfusion to mucosal lesion formation" *Gastrointest. Liver Physiol.*, 1986, pp. G749-G753, vol. 13.

Parr, C. W. "Erythrocyte Phosphogluconate Dehydrogenase Polymorphism" *Nature*, Apr. 30, 1966, pp. 487-489, vol. 210, No. 5035.

Parr, C. W. et al. "Inherited quantitative variations of human phosphogluconate dehydrogenase" *Ann. Hum. Genet.*, 1967, pp. 339-352, vol. 30, No. 4.

Pryor, W. A. et al. "The Inhibitory Effect of Extracts of Cigarette Tar on Election Transport of Mitochondria and Submitochondrial Particles" *Free Radicals in Biology and Medicine*, 1992, pp. 365-372, vol. 12.

Pumphrey, R. E. "Hydrogen Peroxide Proctitis" *American Journal of Surgery*, Jan. 1951, pp. 60-62, vol. 81.

Rady, P. L. et al. "Methylenetetrahydrofolate Reductase (MTHFR): The incidence of Mutations C677T and A1298C in the Ashkenazi Jewish Population" *American Journal of Medical Genetics*, 1999, pp. 380-384, vol. 86.

Rao, S. S. C. et al. "Symptoms and stool patterns in patients with ulcerative colitis" *Gut*, 1988, pp. 342-345, vol. 29.

Reifen, R. et al. "Iron Supplementation May Aggravate Inflammatory Status of Colitis in a Rat Model" *Digestive Diseases and Sciences*, Feb. 2000, pp. 394-397, vol. 45, No. 2.

Ringstad, J. et al. "Serum Selenium, Copper, and Zinc Concentrations in Crohn's Disease and Ulcerative Colitis" *Scand. J. Gastroenterol.*, 1993, pp. 605-608, vol. 28.

Roediger, W. E. W. et al. "Metabolic induction of experimental ulcerative colitis by inhibition of fatty acid oxidation" *Br. J. exp. Pathology*, 1986, pp. 773-782, vol. 67.

Roediger, W. et al. "Human Colonocyte Detoxification" *Gut*, 1997, pp. 731-734, vol. 41, No. 6.

Rosenblatt, D. S. "Inherited Disorders of Folate and Cobalamin Transport and Metabolism" In *The Metabolic & Molecular Bases of Inherited Disease*, 8th edition, Chapter 155, eds. Scriver et al., 1995, pp. 3897-3910 and 3924-3933, McGraw-Hill Medical Publishing Division.

Roth, M. P. et al. "Geographic Origins of Jewish Patients With Inflammatory Bowel Disease" *Gastroenterology*, 1989, pp. 900-904, vol. 97.

Schultz, B. E. et al. "Structures and Proton-Pumping Strategies of Mitochondrial Respiratory Enzymes" *Annu. Rev. Biophys. Biomol. Struct.*, 2001, pp. 23-65, vol. 30.

Schwartz, E. et al. "Letter to the editor" *Digestive Diseases and Sciences*, Jun. 1995, pp. 1290-1291, vol. 40, No. 6.

Shaw, A. et al. "Gas Embolism Produced by Hydrogen Peroxide" *The New England Journal of Medicine*, Aug. 3, 1967, pp. 238-241, vol. 277, No. 5.

Sheehan, J. F. et al. "Ulcerative Colitis Following Hydrogen Peroxide Enema: Case Report and Experimental Production with Transient Emphysema of Colonic Wall and Gas Embolism" *Laboratory Investigation*, 1960, pp. 150-168, vol. 9, No. 1.

Soderholm, J. D. et al. "Chronic Stress Induces Mast Cell-Dependent Bacterial Adherence and Initiates Mucosal Inflammation in Rat Intestine" *Gastroenterology*, 2002, pp. 1099-1108, vol. 123.

Soderholm, J. D. et al. "Stress and the Gastrointestinal Tract II. Stress and intestinal barrier function" *Am. J. Physiol. Gastrointest. Liver Physiol.*, 2001, pp. G7-G13, vol. 280.

Souchard, J. P. et al. "Electron spin resonance detection of extracellular superoxide anion releases by cultured endothelial cells" *Free Radic. Res.*, Nov. 1998, pp. 441-449, vol. 29, No. 5, abstract only.

Srigiridhar, K. et al. "Oral repletion of iron induces free radical mediated alterations in the gastrointestinal tract of rat" *Molecular and Cellular Biochemistry*, 2001, pp. 91-98, vol. 219.

St. Pierre, J. et al. "Topology of Superoxide Production from Different Sites in the Mitochondrial Electron Transport Chain" *The Journal of Biological Chemistry*, Nov. 22, 2002, pp. 44784-44790, vol. 277, No. 47.

Tomlinson, J. E. et al. "Repression of Pentose Phosphate Pathway Dehydrogenase Synthesis and mRNA by Dietary Fat in Rats" *American Institute of Nutrition*, 1988, pp. 408-415, vol. 118, No. 3.

Topping, D. L. et al. "Short-Chain Fatty Acids and Human Colonic Function: Roles of Resistant Starch and Nonstarch Polysaccharides" *Physiological Reviews*, Jul. 2001, pp. 1031-1064, vol. 81, No. 3.

Torisu, T. et al. "A Rare Case of Ulcerative Colitis Complicating Wilson's Disease" *J. Clin. Gastroenterol.*, 2002, pp. 43-45, vol. 35, No. 1.

Turrens, J. F. "Superoxide Production by the Mitochondrial Respiratory Chain" *Bioscience Reports*, 1997, pp. 3-8, vol. 17, No. 1.

Upchurch, G. R. et al. "Homocyst(e)ine Decreases Bioavailable Nitric Oxide by a Mechanism Involving Glutathione Peroxide" *The Journal of Biological Chemistry*, Jul. 4, 1997, pp. 17012-17017, vol. 272, No. 27.

Van Vleet, T. R. et al. "Inhibition of Human Cytochrome P450 2E1 by Nicotine, Cotinine, and Aqueous Cigarette Tar Extract in Vitro" *Toxicological Sciences*, 2001, pp. 185-191, vol. 64.

Venditti, P. et al. "Effects of Thyroid State on $H_2O_2$ Production by Rat Heart Mitochondria: Sites of Production with Complex I- and Complex II-Linked Substrates" *Hormone Metabolic Research*, 2003, pp. 55-61, vol. 35.

Venditti, P. et al. "Effect of thyroid state on lipid peroxidation, antioxidant defences, and susceptibility to oxidative stress in rat tissues" *Journal of Endocrinology*, 1997, pp. 151-157, vol. 155.

Whelan, G. "Epidemiology of Inflammatory Bowel Disease" *Medical Clinics of North America*, Jan. 1990, pp. 1-12, vol. 74, No. 1.

Wilcken, D. E. L. et al. "Relationship Between Homocysteine and Superoxide Dismutase in Homocystinuria—Possible Reference to Cardiovascular Risk" *Arterioscler Thromb Vasc. Biol.*, May 2000, pp. 1199-1202, vol. 20.

"Nicotine Pharmacology" In *Clearing the Smoke: Assessing the Science Base for Tobacco Harm Reduction*. 2001, pp. 243, 267, Chapter 9.

*The Metabolic & Molecular Basese of Inherited Disease*, 8th edition, Chapter 182, eds. Scriver et al., 1995, pp. 4650-4651, McGraw-Hill Medical Publishing Division.

"Management of Ulcerative Colitis" *National Guideline Clearinghouse*: http://www.ngc.gov, 2001, pp. 1-10.

Bailey, S. M. et al. "Ethanol Stimulates the Production of Reactive Oxygen Species at Mitochondrial Complexes I and III" *Free Radical Biology & Medicine*, 1999, pp. 891-900, vol. 27, Nos. 7-8.

Blaut, M. "Assement of bacteria in the gut microbial ecosystem" In *Intestinal flora, European Concerted Action*, 2000, pp. 1-3, Ch. 2.

Huycke, M. M. et al. "In Vivo Production of Hydroxyl Radical by *Enterococcus faecalis* Colonizing the Intestinal Tract Using Aromatic Hydroxylation" *Free Radical & Medicine*, 2002, pp. 818-826, vol. 33, No. 6.

Kehrer, J. P. et al. "The Haber-Weiss reaction and mechanisms of toxicity" *Toxicology*, 2000, pp. 43-50, vol. 149.

Kawai, M. et al. "A case of ulcerative colitis induced by oral ferrous sulfate" *Acta Paediatr. Jpn.*, Aug. 1992, pp. 476-478, vol. 34, No. 4, abstract only.

\* cited by examiner

MATERIALS AND METHODS FOR TREATMENT OF GASTROINTESTINAL DISORDERS

CROSS-REFERENCE TO RELATED APPLICATION

This application claims the benefit of U.S. Provisional Application Ser. No. 60/499,152, filed Aug. 29, 2003.

BACKGROUND OF THE INVENTION

Ulcerative colitis is an inflammatory bowel disease characterized by recurrent bouts of rectal bleeding and bloody diarrhea. The initial inflammatory reaction begins in the rectal mucosa in over 95% of cases and may extend in a contiguous fashion to involve the whole colon (Hendrickson, 2002).

Histologically, ulcerative colitis is manifest by mainly neutrophil infiltration into the colonic mucosal crypts of Lieberkuhn leading to a neutrophilic cryptitis and the formation of micro crypt abscesses, which coalesce to form bleeding macroscopic mucosal ulcerations. Neutrophilic secretion of tissue destructive cytokines and oxygen radicals leads to a chronic crypt destructive colitis that can involve the entire colon (Carpenter, 2000).

Treatment modalities are few and unsatisfactory and remain confined to aminosalicylate derivatives and anti-inflammatory corticosteroids for initial therapy, progressing to potent immunosuppressive agents for recalcitrant disease and finally to colectomy for those patients unresponsive to medical therapy. Most patients with mild to moderate disease have an unpredictable course. Individuals with severe disease comprise approximately 20% of patients. About 85% of patients with severe or fulminant disease will undergo total colectomy within a year. The cumulative likelihood of requiring colectomy by 25 years is about 32%. (National Guidelines Clearinghouse: http://www.ngc.gov "Management of Ulcerative Colitis").

Medical treatment strategies for ulcerative colitis have been directed towards either neutralizing one or more of the cytokines produced by the infiltrating neutrophils or eliminating the source of the cytokine, i.e., the neutrophil itself. Since the history of medically treated ulcerative colitis is characterized by lifelong repeated episodes of the disease, it appears that no currently available medical therapeutic modality is capable of addressing the fundamental disorder present and therefore current therapies are unable to alter the natural history of this condition.

It is perhaps among the greatest physiological wonders of evolution that the most highly evolved immune system ever engendered can remain unperturbed while surrounding the highest concentration of bacteria on the planet, separated only by a tenuous sheet of tissue one cell thick.

This unlikely truce describes the living conditions of the normal human colon where the luminal concentration of potentially pathogenic bacteria is estimated to be $10^{12}$ (one trillion) colony-forming units (viable bacterial cells) per gram of colonic contents (Farrell and Peppercorn, 2002). The number of prokaryotic bacterial cells in the gastrointestinal tract ($10^{14}$) (one hundred trillion) is equal to the total number of cells in the human body (Blaut, 2000; Guyton and Hall, 1997). Close to one half of the weight of feces produced is composed of bacteria and there are over 400 known species of bacteria in the normal human colon, many of which are quite virulent and pyogenic if translocated to other body cavities outside of the intestine.

The mucosal immune system of the gastrointestinal tract can be conceptually divided into a normally non-reactive or tolerant surface component and a potentially reactive sub-surface entity. The surface component, consisting of T-cells interspersed among the colonic epithelial cells, has been rendered tolerant to colonic bacteria. This anergic surface T cell response to normal luminal bacterial flora has been present since birth. Teleologically, these T-cells may serve as a first line defense to recognize foreign bacteria that infect the mucosa itself.

The reactive component of the sub-surface immune system consists of macrophages, B-cells and additional T-cells that reside within the normally sterile environment just beneath the colonic epithelial basement membrane in the lamina propria. These immune cells are physically separated from luminal bacterial antigens by three distinct physical barriers of protection. These consist of, starting from the luminal side, a protective mucus layer, an intact colonic mucosal lining and subjacent basement membrane. This degree of separation maintains a sterile sub-epithelial environment and shields the lamina propria immune cells and vasculature from encountering colonic bacterial products that would otherwise initiate an immune and chemotactic response.

The integrity of the colonic epithelial cell/basement membrane (surface) barrier is paramount in maintaining immune quiescence within the colonic tissues and preventing the colonic immune system from mounting an immune response to the high concentration of bacterial antigen that is poised to invade the normally sterile sub-epithelial environment.

Cellular mechanisms involved in maintaining the integrity of the colonic surface barrier function may therefore be compromised early on in the pathogenesis of ulcerative colitis. Dysfunction of a vital process required to maintain mucosal integrity must therefore be an early and necessary part of a sequential series of events ultimately leading to deterioration of epithelial barrier function with subsequent mucosal immune activation secondary to antigenic penetration into the lamina propria.

In other words, the additive effect of abnormal cellular stressors focused on a common biochemical pathway are acting in concert to disrupt an intracellular biochemical process that contributes a required function necessary for maintaining colonic surface barrier integrity.

The high incidence (over 50%) of spontaneous improvement and relapse seen in ulcerative colitis (Meyers and Janowitz, 1989) suggests a reversible disruption and the possibility of a self replenishing depletion syndrome affecting a crucial element required for mucosal integrity.

Experimental attempts to create an animal model of human ulcerative colitis using rectal instillation of toxic chemicals are inherently limited in their ability to faithfully reproduce the disease due to complex psychological, physiological, genetic, environmental and immunological interactions that antecede and contribute to the pathogenesis of this condition in humans (Farrell and Peppercorn, 2002). In vivo human colonic exposure to toxic chemicals is not currently advocated for any clinical condition. However, such was not always the case.

For many years during the twentieth century hydrogen peroxide enemas were routinely employed and recommended by physicians for the evacuation of fecal impactions. As recently as 1980, hydrogen peroxide enemas were being advocated for the treatment of fecal impaction in a major nursing text (Brunner and Suddarth, 1980). However, in the 1930's reports began to surface regarding the development of rectal bleeding and colitis subsequent to the use of hydrogen peroxide enemas (Benson and Bargen, 1939). A fatal case of colitis subsequent to hydrogen peroxide enema was first recorded in 1948 (Sheenan and Brynjolfsson, 1960). In this case, the authors report a 41-year-old white female who died 5 days after self-administration of a hydrogen peroxide enema to relieve a fecal impaction. The autopsy report noted acute ulcerative colitis, which was "attributed to the action of the hydrogen peroxide enema." Since then there have been reports of fatal outcomes secondary to the development of colitis subsequent to the use of hydrogen peroxide enemas. In 1951, Pumphrey reports severe ulcerative proctosigmoiditis following hydrogen peroxide enemas in two patients (Pumphery, 1951). In 1967, Shaw reported the deaths of several infants some time following the evacuation of impacted meconium with hydrogen peroxide (Shaw et al., 1967). In 1981, Meyer et al. reported three cases of acute ulcerative colitis after administration of hydrogen peroxide enema and stated that "acute ulcerative colitis appears to be a fairly predictable occurrence after hydrogen peroxide enemas" (Meyer et al., 1981). In 1989, Bilotta and Waye describe an epidemic of hydrogen peroxide induced colitis in the G.I. endoscopy unit at their institution. This was due to the inadvertent instillation of hydrogen peroxide during colonoscopy. Upon contact of the hydrogen peroxide with colonic mucosa they visualized instantaneous mucosal whitening and frothy bubbles, which they describe as the "snow white" sign (Bilotta and Waye, 1989). In 1995, inadvertent colonic instillation of hydrogen peroxide during colonoscopy resulted in the same mucosal reaction (Schwartz et al., 1995). In 2001, rectal bleeding was, once again, noted to be a complication of hydrogen peroxide enemas (Thibaud et al., 2001).

In their classic experiments, Sheehan and Byrnjolfsson (1960) produced acute and chronic ulcerative colitis by rectal injection of rats with a 3% solution of hydrogen peroxide. Microscopic examination of sacrificed rats revealed colonic mucosal ulceration and neutrophilic infiltration, which was "sharply delineated from adjacent normal mucosa." The mucosal inflammation, which reached 5 cm above the anus at 5 hours after injection had extended proximally to 9 cm by one week. Additionally the authors noted that, in surviving rats, most of the colonic mucosal ulcerations were healed by 10 weeks with the exception of some, which "were located almost always in the left colon a few centimeters above the anus."

Hydrogen peroxide is a colorless, heavy, strongly oxidizing liquid, a powerful bleaching agent; also used for wastewater treatment, as a disinfectant and as an oxidant in rocket fuels. Hydrogen peroxide ($H_2O_2$) also has a ubiquitous presence in cells and is continuously being generated in the cytosol and several different sub-cellular organelles including peroxisomes, endoplasmic reticulum and nucleus by various oxidase and oxygenase enzymes (i.e. xanthine oxidase, cytochrome p450 oxygenase) (Chance et al., 1975). However, in most cells, approximately 90% of hydrogen peroxide is generated as a toxic by-product of mitochondrial electron transport chain respiratory activity (Eaton and Qian, 2002).

The mitochondrial electron transport chain (ETC) consists of five distinct protein components, which are embedded within the mitochondrial inner membrane facing the inner liquid matrix. Three of these components are large, membrane fixed, protein complexes (Complex I, III and IV), which serve as trans-membrane redox linked proton pumps that act to transfer protons from the matrix through the inner membrane into the inter-membrane space (Schultz and Chan, 2001). These three complexes interact with two smaller mobile carriers (complex II and cytochrome c), which shuttle electrons between the complexes. Complex II (Succinate dehydrogenase, EC 1.3.5.1) transfers electrons between Complex I (NADH dehydrogenase EC 1.6.5.3) and complex III (Ubiquinol-cytochrome c reductase, EC 1.10.2.2) while cytochrome c (a small heme containing protein) shuttles electrons from complex III to complex IV (Cytochrome-c oxidase, EC 1.9.3.1). These redox electron transfers result in conformational changes of the inner membrane-bound protein complexes (I, II and III), which drive the flow of protons from the matrix through the inner membrane and into the inter membrane space. The resultant accumulation of protons within the inter membrane space creates an electrochemical gradient, which drives the flow of these protons back into the matrix through a trans-membrane enzyme (ATP synthase, EC 3.6.1.34 or Complex V). It is the energy provided by this retrograde flow of protons down its electrochemical gradient, which provides the energy for ATP synthase to synthesize ATP (Schultz and Chan, 2001). The final acceptor of electrons in the chain is diatomic (molecular) oxygen, which is completely reduced to water by Cytochrome-c oxidase (complex IV) in a reaction in which molecular oxygen ($O_2$) combines with 4 electrons ($e^-$) and 4 protons (H+) to produce two molecules of water ($H_2O$). Complex I and III are the source of electron leakage leading to the eventual intracellular generation of hydrogen peroxide (Lemasters and Nieminen, 2001; St.-Pierre et. al., 2002).

There are thousands of these electron transport chain protein complexes doting the matrix aspect of mitochondrial cristae, which continuously reduce oxygen in order to build the electrochemical potential needed to create a chemiosmotic gradient of protons in the intermembrane space that drives the synthesis of adenosine triphosphate (ATP).

The transfer of electrons through the electron transport chain, however, is not perfect and up to 5% of electrons do not make it all the way through the chain and fail to combine with oxygen to produce water (Liu, 1997; Turrens, 1997; Eberhardt, 2001). Electron transfer through the ETC depends upon requisite conformational changes and proton transfers which must occur prior to the electron passing to the next protein in the chain. Failure of these changes to take place leads to a decoupling of electron transfer referred to as an electron leak (Schultz and Chan, 2001). These "leaked" electrons, from complex I and III of the electron transport chain, combine directly with molecular oxygen in the immediate vicinity, instead of the next carrier in the chain, to form superoxide ($O_2^-$.) which is the first (single electron) incomplete reduction product of molecular oxygen (Cadenas and Davies, 2000). The extra unpaired electron in its outer valence orbital makes superoxide a radical, also commonly referred to as a reactive oxygen metabolite (ROM) or species (ROS). It is estimated that 2% of available oxygen is converted to superoxide by electron transport chain "leakage" (Boveris and Chance, 1973). At physiological pH superoxide exists as an anion radical and acts preferentially as a reducing agent (donate an electron) (Eberhardt, 2001). Superoxide can cause serious damage to cells if allowed to accumulate.

Superoxide, however, due to its negative charge, cannot pass through biological membranes and is contained within the mitochondria. Superoxide can spontaneously dismutate to hydrogen peroxide or undergo enzymatic dismutation to hydrogen peroxide ($H_2O_2$) at the site of production within mitochondria by the enzyme superoxide dismutase (SOD) (EC 1.15.1.1) (Chance 1979, Eberhardt, 2001). In this enzymatic reaction two superoxide molecules are combined with two protons and converted to one molecule of hydrogen peroxide and one molecule of diatomic oxygen, ($O_2^-\cdot + O_2^-\cdot \rightarrow SOD$, $2H^+ \rightarrow H_2O_2 + O_2$). Superoxide is considered to be a stoichiometric precursor of mitochondrial hydrogen peroxide (Chance et al., 1979; Han et al., 2001) such that virtually all superoxide radicals generated in mitochondria are converted to hydrogen peroxide while channeling 2% of total mitochondrial oxygen consumption, via superoxide, into the formation of $H_2O_2$ (Han et al., 2001; Boveris et al., 1972).

Superoxide and hydrogen peroxide are considered the primary reactive oxygen metabolites. All other radicals are generated by way of secondary reactions of these initially formed reactive oxygen metabolites (Eberhardt, 2001). Within mitochondria superoxide, therefore, is an intermediary in the formation of hydrogen peroxide.

Hydrogen peroxide is unique among reactive oxygen metabolites. It is not a radical, as it has no unpaired electrons however; it is considered a ROM because it is the immediate precursor of the most damaging and chemically reactive radical known which is the hydroxyl radical (.OH). Hydrogen peroxide can undergo a one-electron reduction to form hydroxyl radical. The reducing agent (electron donating species) can be a transition metal ion (Fenton reaction) or the superoxide radical (Haber-Weiss reaction).

Both iron and copper ions (present in tissues) can act as reducing agents in a Fenton reaction ($Fe^{+2} + H_2O_2 \rightarrow Fe^{+3} + HO^- + HO\cdot$) or ($Cu^+ + H_2O_2 \rightarrow Fe^+3 + HO^- + HO\cdot$) in the homolytic fission of hydrogen peroxide to hydroxyl radical and a hydroxide anion.

The Haber-Weiss reaction ($O_2^-\cdot + H_2O_2 \rightarrow O_2 + HO^- + HO\cdot$) can also be accelerated in vivo when iron is present in an iron catalyzed Haber-Weiss reaction ($O_2^-\cdot + Fe^{+3} \rightarrow O_2 + Fe^{+2}$) followed by the classic Fenton reaction above (Eberhardt, 2001). Superoxide, in addition to being generated within the cell, is also released to the extracellular compartment from various sources including fibroblasts, endothelial cells and intestinal bacteria (O'Donnell et al., 1996; Souchard et al., 1998; Huycke et al., 2002; Huycke and Moore, 2002; Huycke et al., 2001). In biological systems, however, the iron catalyzed Haber-Weiss reaction is considered the major mechanism by which the highly reactive hydroxyl radical is generated (Kehrer, 2000).

The hydroxyl radical is an extraordinarily powerful oxidizing agent, which attacks other molecules at diffusion-limited rates and will indiscriminately destroy everything it encounters (Eberhardt, 2001; Fridovich, 1998; Chen and Schopfer, 1999). The hydroxyl radical is the most chemically reactive oxygen species formed in cellular metabolism and is principally responsible for the cytotoxic effects of oxygen in animals (Chen and Schopfer, 1999). Despite its immensely damaging biological effects the hydroxyl radical is continuously produced with relative ease (Fridovich, 1998). This no doubt is due to the constitutive nature of its precursor ($H_2O_2$), the ubiquitous distribution of transition metal catalyst (iron and copper) necessary for its generation and the abundance of superoxide radical serving as the initial electron donating (reducing) species.

Reacting at diffusion controlled rates means that hydroxyl radical will react at every collision each time it encounters another molecule. Because of its extreme reactivity the hydroxyl radical will react with most molecules in a site specific manner via addition and abstraction and, therefore, most molecules serve as scavengers of hydroxyl radical (Eberhardt, 2001).

Molecules interacting with hydroxyl radicals sustain severe damage to the extent that the hydroxyl radical is able to crack polysaccharides, nucleic acids, and proteins located just a few atomic diameters (nanometers) from its site of generation (Chen and Schopfer, 1999).

The diffusion limited reaction rate of hydroxyl radical gives it the shortest half-life of any reactive oxygen metabolite (one nanosecond) (Kehrer, 2000). This extremely short reaction time makes the hydroxyl radical very difficult to scavenge with any specific antioxidant molecule. Detoxification of hydrogen peroxide, the immediate precursor to hydroxyl radical, therefore is crucial to normal cellular function and survival. Consequently, very sophisticated intracellular enzymatic antioxidant mechanisms are in place to neutralize hydrogen peroxide at its site of generation before it can accumulate within cellular compartments. These $H_2O_2$ neutralizing antioxidant enzymes are catalase (E.C. 1.11.1.6) and glutathione peroxidase (E.C. 1.11.1.9). The fact that there are two enzyme systems for $H_2O_2$ neutralization suggests that removal of hydrogen peroxide is essential for survival of the cell.

Catalase is located mainly within peroxisomes while glutathione peroxidase is found throughout the cytoplasm and mitochondria (Eberhardt, 2001, pg 286; Davies, 2000; Cadenas and Davies, 2000). The compartmentalization of catalase coupled with a lower Km for $H_2O_2$ and a first order catalytic reaction which is strictly proportional to the $H_2O_2$ concentration suggests that glutathione peroxidase is more important for the removal of $H_2O_2$ than catalase (Eberhardt, 2001, pg. 125).

A degradation profile for $H_2O_2$ has been established in human Jurkat T cells. This study determined that glutathione peroxidase activity is responsible for 91% of $H_2O_2$ consumption while catalase only contributes a minor role at 9% (Boveris and Cadenas, 2000). The relative importance of these enzymes is manifested by the consequences of their respective deficiency states. Acatalasemia in humans is a relatively benign disease and most patients with this condition have no serious pathology.

Experimental acatalasemic mice likewise have no spontaneous health problems (Eaton and Ma, 1995). Complete absence of glutathione peroxidase, in contrast, has not been reported in humans, presumably because the lack of this crucial enzyme precludes embryogenesis.

On a populational level, ethnic variation of glutathione peroxidase has been recorded with individuals of Jewish or Mediterranean origin exhibiting lower activities (*The Metabolic and Molecular Basis of Inherited Disease*, 2001, 8th ed., p. 4650). A two to four fold increase in incidence and prevalence of ulcerative colitis has also been reported for these ethnic groups (Roth et al., 1989).

As can be understood from the above, there remains a need in the art for therapeutic modalities to treat inflammatory bowel diseases such as ulcerative colitis.

BRIEF SUMMARY OF THE INVENTION

The subject invention concerns materials and methods for the prevention and treatment of gastrointestinal diseases. One aspect of the invention concerns methods and compositions for treatment of inflammatory bowel disorders, such as Crohn's disease and ulcerative colitis. In one embodiment, a therapeutic composition of the present invention comprises a reducing agent. In an exemplified embodiment, the reducing agent is sodium thiosulfate. In one embodiment, a therapeutic composition of the invention comprises sodium thiosulfate, bismuth subgallate, vitamin E, and sodium cromolyn. In an exemplified embodiment, a therapeutic composition is provided in a form suitable for administration as a retention enema.

The subject invention also concerns methods of treating a person or animal having an inflammatory bowel disorder. In one embodiment of the subject methods, a person or animal in need of treatment is administered a composition of the present invention in a biologically compatible form or composition. In one embodiment, a composition to be administered comprises a reducing agent such as sodium thiosulfate. In an exemplified embodiment, the therapeutic composition is administered rectally.

The subject invention also concerns kits and containers comprising a therapeutic composition or compounds of the present invention. The containers can be selected for ease of administration of a therapeutic composition to a person or animal.

The subject invention also concerns methods and kits for detecting and diagnosing an inflammatory bowel disorder, such as ulcerative colitis.

DETAILED DISCLOSURE OF THE INVENTION

The subject invention concerns materials and methods for the prevention and treatment of gastrointestinal diseases. One aspect of the invention concerns methods and compositions for treatment of inflammatory bowel disorders, such as Crohn's disease and ulcerative colitis, and irritable bowel disorder. It has been discovered that the production of hydrogen peroxide ($H_2O_2$) and its overproduction and escape from cells of the gastrointestinal tract is a causal component of inflammatory bowel disorders such as ulcerative colitis. The cells of the body are constantly producing oxygen radicals, including hydrogen peroxide, as a by-product of metabolism. These radicals must be neutralized within the cells before they can damage intracellular structures and lead to cell death. The constant generation of oxygen radicals and hydrogen peroxide is an oxidative stress that is neutralized by the reducing capacity of the cell. The most important reducing substance within cell is glutathione. Thus, the reducing environment that cells require in order to function is maintained by a delicate balance between the reduction capacity of the cell (mainly glutathione) and oxygen radicals (mainly hydrogen peroxide). Under normal conditions the intracellular hydrogen peroxide concentration is maintained very low by the constant production of glutathione which neutralizes (reduces) $H_2O_2$. When this balance is disturbed either by increased $H_2O_2$ generation, decreased glutathione production or both, then hydrogen peroxide will accumulate within cells and diffuse through the cellular membrane to the extracellular space. When this occurs in the rectal tissues, the colonic barrier to luminal bacterial products is disrupted allowing tissue penetration of antigenic material into the normally sterile colonic lamina propria. The subsequent infiltration of activated neutrophils results in secretion of enormous amounts of tissue destructive cytokines and additional oxygen radicals including hydrogen peroxide. Thus, a vicious cycle is set up whereby cryptal neutrophils, upon exposure to fecal material, are stimulated to produce destructive cytokines and oxygen radicals in an attempt to rid the local environment of bacteria, which further damages the colonic tissue barrier thereby allowing additional bacterial infiltration with amplification of the immune response and so on until the entire colon is involved. The production of hydrogen peroxide by infiltrating neutrophils is able to diffuse into adjacent normal colonic tissue, overwhelming its reducing capacity and causing oxidative damage to adjacent colonic barrier function and epithelial cells. This results in a contiguous spread of inflammation from the point of origin in the rectum to the rest of the colon. Hydrogen peroxide that has diffused or escaped from a cell can be converted to a hydroxyl radical which can subsequently disrupt cellular structures such as the basement membrane and tight junctions. This initiates the immune response which results in the pathology associated with ulcerative colitis.

Ulcerative colitis can be divided into two phases. The first phase is called induction and begins with the extracellular diffusion of hydrogen peroxide to the extracellular environment. Throughout this phase the epithelial lining appears macroscopically intact and histologically normal. The damage is confined to molecular disruption of colonic epithelial tight junctions and basement membranes resulting in transitory increased colonic permeability to intestinal antigens. There is no rectal bleeding during this phase and this process may go on for months to years resulting in sporadic extra intestinal manifestations such as myalgias, arthralgias and faciitis due to intermittent immune activation subsequent to transitory colonic sub-mucosal antigenic penetration. Due to the high colonic epithelial turnover rate of about three days it is possible to repair the damage and restore the colonic barrier if the initial damage is not overwhelming. However, if the epithelial barrier cannot be reassembled and antigenic invasion is sustained, then further immune activation in the form of neutrophilic infiltration will occur.

The second phase of ulcerative colitis begins with neutrophilic invasion into the colonic tissues and is called the propagation phase. It is during this phase that neutrophil derived cytokines and oxygen radicals initiate tissue damage leading to mucosal ulceration and rectal bleeding and diarrhea characteristic of this disease.

The importance of two distinct phases of ulcerative colitis lies in the ability to modify the inflammatory process during the induction phase via manipulation of risk factors which can be positive (pro-inflammatory, increasing $H_2O_2$ production) or negative (anti-inflammatory, decreasing $H_2O_2$ production). The propagation phase, as the name implies, is self-sustaining and auto-stimulating, and is not affected by risk factors. It is during the propagation phase that individuals manifest rectal bleeding due to colonic tissue destruction and without external intervention to reverse the process may develop extensive colonic inflammation leading to colectomy. Colectomy will eliminate the source of induction and propagation along with that segment of intestine having a damaged and permeable barrier. This will abolish the portal of systemic antigenic entry and terminate the inflammatory process. However, colonic inflammation can be terminated anytime during induction if risk factors promoting $H_2O_2$ production are recognized and eliminated. Propagation can also be terminated by appropriate intervention to treat a patient with methods and compositions of the present invention.

Any materials that can be used to neutralize hydrogen peroxide or its decomposition products (hydroxyl radical or hydroxide anion) are contemplated within the scope of the invention. These include, but are not limited to, oxidizing agents, reducing agents, enzymes such as glutathione peroxidase and catalase, catalysts (such as zinc dust or other metal powders or metal catalysts), manganese in a bicarbonate buffer, and asbestos fibers or other fibers able to decompose hydrogen peroxide. Glutathione, or its precursor amino acids (glycine, cysteine and glutamate) can also be used in the compositions and methods of the invention. Monoester or diester glutathione derivatives can be used with the subject invention as glutathione with ester groups attached is taken up into cells more readily than glutathione.

In one embodiment, a therapeutic composition of the present invention comprises a reducing agent. In an exemplified embodiment, the reducing agent is a thiosulfate ion, which can be provided in the form of a salt such as, for example, sodium thiosulfate, ammonium thiosulfate, calcium thiosulfate, potassium thiosulfate, silver thiosulfate, choline thiosulfate, gold sodium thiosulfate, magnesium thiosulfate hex hydrate, and thiosulfate hyposulfite. Examples of other reducing agents contemplated within the scope of the invention include, but are not limited to, metal borohydrides, sodium hydrosulfite, dimethylthiourea, sodium bisulfite, thiourea dioxide, diethylhydroxylamine, zinc dust, sodium cyanoborohydride, sodium hydride, trimethyl borate, benzyl triphenphosphonium chloride, butyl triphenphosphonium bromide, ethyl triphenphosphonium acid acetate, ethyl triphenphosphonium bromide, ethyl triphenphosphonium iodide, ethyl triphenphosphonium phosphate, and tetrabutyl phosphonium acid acetate. Another reducing agent that can be used is glutathione, or a monoester or diester glutathione, diester glutathione or multiester glutathione derivative. A therapeutic composition of the present invention can optionally include one or more of the following:

1) a compound or composition that is antibacterial or that prevents or inhibits adherence of bacteria to gastrointestinal tissues or cells. In one embodiment, the compound can be a bismuth salt. In an exemplified embodiment, the compound can be bismuth subgallate. Antibiotics active against bacteria present in the gastrointestinal tract can be included. In a preferred embodiment, the compound is active against Bacteroides.

2) a compound or composition that adds viscosity (for steric hindrance) and/or that inhibits epithelial lipid peroxidation, such as, for example, d-alpha-tocopherol (vitamin E), carboxymethylcellulose or other viscous mono or polysaccharide compounds (e.g., honey).

3) a compound or composition that inhibits mast cells and/or that helps to seal or repair tight junctions between cells in the gastrointestinal tract. In one embodiment, the compound can be sodium cromolyn.

4) a compound or composition that scavenges hydroxyl radicals. In one embodiment, the compound can be dimethyl sulfoxide (DMSO), mannitol, methional, deoxyribose or DMPO (5,5-dimethylpyrollidine-N-oxide).

5) a compound or composition that inhibits or blocks NADPH oxidase, such as DMSO or apocynin.

6) a compound or composition that kills or inhibits colonically localized neutrophils, or that prevents or inhibits neutrophils from entering the colon or exiting the colonic vasculature. In one embodiment, antibodies or other blocking agents of vascular adhesion molecules (ICAMS) present on vascular endothelium, such as selectin, or antibodies or other blocking agents of the corresponding neutrophilic counter ligand, such as integrin, can be used.

7) a compound or composition that stops or inhibits neutrophils from producing hydrogen peroxide. Examples include DMSO and Trental.

8) a compound or composition that chelates or sequesters iron molecules that are necessary for the reduction of hydrogen peroxide to a hydroxyl radical. In one embodiment, the iron chelating agent Desferal (Deferoxamine) can be used.

9) the compound 5-aminosalicylic acid (5-ASA) or colazal (balsalazide disodium) can be included.

10) a compound that neutralizes or scavenges hydroxide ions. In one embodiment, a composition of the invention can comprise a weak acid or weak base, such as in the form of a buffered solution at a pH of from about 6.8 to about 7.4 comprising sodium bicarbonate.

11) any agent or therapy that will raise oxygen tension in the lumen of the colon or that suppresses cytochrome oxidase enzyme.

In one embodiment, a composition of the invention comprises a reducing agent and an NADPH-oxidase inhibitor. Preferably, the reducing agent is a thiosulfate salt, such as sodium thiosulfate, and the NADPH-oxidase inhibitor is apocynin. In a preferred embodiment, the composition is provided in an orally administered capsule that delays dissolving until it is present in the colon.

The compounds of the invention can be administered as a single composition, or they can be administered individually at the same or different times and via the same or different route (e.g., oral, rectal, etc.) of administration. In one embodiment, a composition of the invention is provided in a mixture or solution suitable for rectal instillation and comprises sodium thiosulfate, bismuth subgallate, vitamin E, and sodium cromolyn. In one embodiment, a therapeutic composition of the invention comprises, in a suppository form, butyrate, and glutathione monoester, glutathione diethylester or other glutathione ester derivatives. The suppository can optionally include sodium thiosulfate and/or vitamin-E.

The subject invention also concerns methods of treating a person or animal having an inflammatory bowel disorder, such as, for example, ulcerative colitis. In one embodiment of the subject methods, a person or animal in need of treatment is administered an effective amount of a therapeutic composition of the present invention in a biologically compatible form or composition. In an exemplified embodiment, the reducing agent of the composition is a thiosulfate salt such as, for example, sodium thiosulfate. In one embodiment, the therapeutic composition is administered rectally or by delayed dissolving oral capsule. Delayed dissolution dosage forms include pH-dependent capsules and coatings that only dissolve at the pH associated with the colonic environment. Examples of pH-dependent materials include, but are not limited to, methyl methacrylate, methacrylic acid and/or ethyl acrylate polymers, including for example, ammonio methacrylate copolymer. Other dosage forms for delivery of a composition of the invention to the colon include, for example, time-dependent delivery systems, pressure-dependent delivery systems, bacterial-dependent systems (Basit et al., 2003). Also contemplated are dosage forms that utilize oxidation potential-dependent systems. Colon content has a much higher oxidative potential than the small intestinal contents since many times more bacteria are present in the colon. An oxidation potential-dependent system is a delivery system that is sensitive to oxidation potential and releases its contents or becomes active when the capsule is exposed to the higher oxidation level in the colon. This can be in the form of a prodrug which is degraded to the active drug when oxidized and capsules which dissolve when exposed to the high level of oxidation in the colon. In one embodiment, a combination of rectally and orally administered compositions are given to a patient, particularly if the patient has rectal bleeding. After bleeding is controlled, rectal therapy can optionally be discontinued and oral therapy maintained as necessary. Thiosulfates, such as sodium thiosulfate can optionally be administered in a solution intravenously, e.g., solutions of from about 10% to about 25% (w/v) sodium thiosulfate can be given. Methods of the present invention also contemplate institution of lifestyle changes of the patient, as described herein, either alone or in conjunction with the use of therapeutic compositions of the invention.

Dosage ranges for the various compounds to be administered to an individual patient can be determined by an ordinarily skilled clinician. Examples of dosage ranges provided herein are for guidance and should not be construed as limiting the scope of the invention in regard to dosages that can be administered. Dosage ranges can be, for example:

sodium thiosulfate: 150-250 mg/kg body weight
bismuth subgallate: 2-4 mg/kg body weight
vitamin E: 25-30 IU/kg body weight
cromolyn sodium: 1-3 mg/kg body weight The above components can be prepared in a retention enema in sterile water according to the following:

Step 1: Dissolve sodium thiosulfate in water by gently shaking until all crystals are dissolved.

Step 2: Add cromolyn sodium until completely dissolved.

Step 3: Add bismuth subgallate and gently shake until completely suspended.

Step 4: Add vitamin E and shake until suspended.

The methods of the present invention also include oral administration of a drug that lowers endogenous catecholamines, such as clonidine, where such treatment is indicated by the symptoms and risk factors presented by the patient. Monoamine oxidase (MAO) inhibitors that inhibit or prevent mitochondrial MAO from metabolizing endogenous catecholamines can also be administered as part of a patient treatment regimen and is contemplated within the scope of the present invention. Preferably, the MAO inhibitor is one that does not pass through the blood-brain barrier. In one embodiment of the invention, a combination of clonidine (or a similar drug) and an MAO inhibitor is administered to a patient.

Also contemplated within the scope of the invention is the administration of NADPH-oxidase inhibitors, such as Trental (pentoxifylline) and apocynin; these can be administered as a delayed dissolving oral capsule that dissolves in the colon, or as a rectal solution. Pentoxifylline has anti-inflammatory activity and may function as a purinergic agonist via an adenosine receptor on the surface of the infiltrating neutrophil which can inhibit NADPH oxidase and apoptosis. This oral therapy can be continued, along with lifestyle changes, as maintenance therapy to prevent re-induction and relapse.

In one embodiment, a composition of the invention comprises a reducing agent and an NADPH-oxidase inhibitor. Preferably, the reducing agent is a thiosulfate salt, such as sodium thiosulfate, and the NADPH-oxidase inhibitor is apocynin. In a preferred embodiment, the composition is provided in an orally administered capsule that delays dissolving until it is present in the colon. Delayed dissolution dosage forms include pH-dependent capsules and coatings that only dissolve at the pH associated with the colonic environment. Examples of pH-dependent materials include, but are not limited to, methyl methacrylate, methacrylic acid and/or ethyl acrylate polymers, including for example, ammonio methacrylate copolymer. Other dosage forms for delivery of a composition of the invention to the colon include, for example, time-dependent delivery systems, pressure-dependent delivery systems, bacterial-dependent systems (Basit et al., 2003). Also contemplated are dosage forms that utilize oxidation potential-dependent systems.

The methods and compositions of the present invention can be used with humans and other animals. The other animals contemplated within the scope of the invention include domesticated, agricultural, or zoo- or circus-maintained animals. Domesticated animals include, for example, dogs, cats, rabbits, ferrets, guinea pigs, hamsters, pigs, monkeys or other primates, and gerbils. Agricultural animals include, for example, horses, mules, donkeys, burros, cattle, cows, pigs, sheep, and alligators. Zoo- or circus-maintained animals include, for example, lions, tigers, bears, camels, giraffes, hippopotamuses, and rhinoceroses.

Compounds useful in the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the compound is combined with a suitable carrier in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically acceptable carriers and diluents which are known to those skilled in the art. Examples of carriers or diluents for use with compounds include ethanol, dimethyl sulfoxide, glycerol, alumina, starch, and equivalent carriers and diluents. To provide for the administration of such dosages for the desired therapeutic treatment, new pharmaceutical compositions of the invention will advantageously comprise between about 0.1% and 45%, and especially, about 1 and 15% by weight of the total of one or more of the compounds based on the weight of the total composition including carrier or diluent.

The subject invention also concerns dosage forms of the compounds and compositions of the invention. In one embodiment, compounds and compositions are provided in orally or rectally administered dosage forms. A dosage form for oral administration comprising a capsule that dissolves in the colon and containing an effective amount of i) a reducing agent, for example, sodium thiosulfate, and ii) an NADPH-oxidase inhibitor, for example, apocynin, is specifically contemplated in the present invention. Delayed dissolution dosage forms include pH-dependent capsules and coatings that only dissolve at the pH associated with the colonic environment. Examples of pH-dependent materials include, but are not limited to, methyl methacrylate, methacrylic acid and/or ethyl acrylate polymers, including for example, ammonio methacrylate copolymer. Other dosage forms for delivery of a composition of the invention to the colon include, for example, time-dependent delivery systems, pressure-dependent delivery systems, bacterial-dependent systems (Basit et al., 2003). Also contemplated are dosage forms that utilize oxidation potential-dependent systems.

The compounds of the subject invention can also be administered utilizing liposome technology, slow release capsules, implantable pumps, biodegradable containers and other means known in the art. These delivery vehicles and methods can, advantageously, provide a uniform dosage over an extended period of time.

The subject invention also concerns containers comprising a therapeutic composition of the present invention. The containers can be selected for ease of storage and/or administration of a composition to a person or animal, e.g., a container can be one suitable for use in rectal administration of a therapeutic composition. The containers can be composed of any suitable material, including glass, plastic, etc. and can be disposable and/or recyclable. Therapeutic compositions of the present invention are preferably provided as a sterile composition in a sterile container. The subject invention also concerns kits comprising, in one or more containers, a therapeutic composition or compound of the invention. In one embodiment, a kit of the invention comprises, in one or more containers, a reducing agent, an antibacterial and/or antiadherence agent, a viscosity enhancing and/or lipid peroxidation inhibitor, and a mast cell inhibitor and/or an agent that repairs, seals, or regenerates tight junctions between cells, e.g., an epidermal growth factor (EGF). In an exemplified embodiment, the kit comprises the compounds sodium thiosulfate, bismuth subgallate, vitamin E, and sodium cromolyn. The compounds of the invention can be provided in a kit in a single pre-mixed dosage form, or in individual dosage units that are mixed together prior to administration, or that are administered individually.

The subject invention also concerns methods for detecting and diagnosing ulcerative colitis, and diagnostic kits for the same. Any means for detecting or measuring a physiological parameter associated with the induction phase or the propagation phase of ulcerative colitis as described herein is contemplated within the scope of the present invention. In one embodiment, rectal tissue is screened for the presence of increased levels of hydrogen peroxide, decreased levels of glutathione, or both. Techniques and materials for detecting or quantitating hydrogen peroxide and glutathione are known in the art. In another embodiment, colonic tissue is screened for the infiltration of activated neutrophils and/or the presence of neutrophil-derived cytokines or products of lipid peroxidation. Techniques and materials for detecting or quantitating activated neutrophils and neutrophil-derived cytokines are known in the art. Assays of the invention can optionally include controls, both positive and negative, and/or other standards (e.g., normal rectal tissue or cells; standard or normal concentration of hydrogen peroxide; standard or normal concentration of glutathione, etc.) for evaluation with the results of a tested sample. Assays screening for multiple physiological parameters associated with ulcerative colitis are included within the scope of the present invention. Tissue to be used for the assays of the present invention can be local (e.g., rectal tissue) or systemic (e.g., blood, lymph, etc.). The diagnostic assays of the invention can be invasive or non-invasive. The diagnostic assays can provide evidence of oxidative risk (risk of entering the induction phase of ulcerative colitis), of oxidative stress (in the induction phase), and of oxidative damage (pre-propagation phase).

The subject invention also concerns a method for assessing an individual's risk of developing ulcerative colitis or determining what stage of the disease the patient is in. The method comprises assaying for $H_2O_2$, glutathione, and exposure time parameters, and then determining an individual's oxidative risk ($R_{ox}$) index based upon the following formula:

$$R_{ox} = \frac{(H_2O_2 \text{ level})(\text{tissue exposure time})}{(\text{glutathione level})}$$

wherein $H_2O_2$ level—Refers to colonic epithelial $H_2O_2$ level which may be determined directly or indirectly.

Tissue exposure time—Determined by the colonic epithelial turnover rate. This is the time epithelial cells are exposed to damaging oxygen radicals including $H_2O_2$.

Glutathione level—Refers to the amount of cytoprotective intracellular glutathione available to colonic epithelial cells to neutralize hydrogen peroxide.

$R_{ox}$—A global measure of the oxidative stress level a tissue or organism is subjected to. The higher the $R_{ox}$ the greater the risk of developing oxidative medicated tissue damage such as ulcerative colitis.

Assays for determining each of the parameters of the formula are described herein. The $R_{ox}$ value can be used to assess whether an individual is 1) at risk of entering the induction phase of ulcerative colitis, 2) is in the induction phase of ulcerative colitis, or 3) is at risk of entering the propagation phase of ulcerative colitis.

Assays Related to Levels of $H_2O_2$ Include:

1. Tests that directly or indirectly measure intracellular or extracellular colonic hydrogen peroxide, hydroxyl radical or hydroxide ion. Hydrogen peroxide can be assayed in the feces, in rectal biopsy tissue, urine, and the blood. Hydrogen peroxide is the final common pathway for the formation of all hydroxyl (and hydroxide) which are the elements that cause tissue damage. The hydrogen peroxide level is a direct indicator of the potential for oxidative tissue damage. Thus, any condition that increases $H_2O_2$ will increase the $R_{ox}$.

2. Tests that directly or indirectly measure the activity of colonic glutathione peroxidase (GPx) enzyme. GPx is the major enzyme that degrades hydrogen peroxide and hydrogen peroxide will increase with decreased GPx activity.

3. Tests that directly or indirectly measure colonic epithelial cell lipid membrane peroxidation. Lipid peroxidation in ulcerative colitis is caused by the effect of hydroxyl radical on the colonic epithelial cell.

4. Tests that directly or indirectly measure colonic epithelial cell proliferation. Hydrogen peroxide induces colonic epithelial cells to multiply. This is manifested by the presence of Melanosis Coli which is a dark lipid pigment which accumulates in cells that are rapidly dividing. It looks like black spots on the colonic mucosa. Thus, assays that measure melanosis coli are contemplated by the invention.

5. Tests that directly or indirectly measure colonic epithelial cell nuclear DNA oxidation. Hydrogen peroxide can also diffuse into the nucleus and oxidize the DNA. These oxidation products can be measured and provide an estimate of oxidative stress.

6. Tests that directly or indirectly measure colonic epithelial cell mitochondrial DNA damage. Hydrogen peroxide is produced in the mitochondria and will damage mitochondrial DNA before any other structure.

7. Tests that directly or indirectly measure protein carbonyl groups since hydrogen peroxide can oxidize proteins. Also, tight junction protein remnants would be found in feces if oxidized and damaged. The tight junctions and intracellular enzymes are made of proteins.

8. Tests that directly or indirectly measure colonic epithelial cell superoxide levels. Superoxide is the immediate precursor of hydrogen peroxide. If superoxide is elevated then hydrogen peroxide will be elevated.

9. Tests that directly or indirectly measure colonic epithelial cell superoxide dismutase activity. Superoxide dismutase is the enzyme that converts superoxide to hydrogen peroxide. If its activity is increased then hydrogen peroxide will increase.

10. Tests that directly or indirectly measure electron transport activity. Electron transport activity is responsible for hydrogen peroxide production. If electron transport activity could be measured this would be an indirect reflection of hydrogen peroxide production. Electron transport activity is mainly responsible for an individual's basal metabolic rate (BMR). When metabolism is increased the electron transport activity is increased and more hydrogen peroxide is produced.

11. Tests that directly or indirectly measure colonic epithelial cell apoptosis. Hydrogen peroxide causes single cell death called apoptosis. These cells would slough off into the feces. In one embodiment, apoptosis is measured from fecal samples or colonic biopsies.

Assays Related to Time of Exposure:

1. The turnover of colonic epithelial cells is about 3 days. This can be accelerated by epidermal growth factor. Any condition that decreases EGF or its receptors on the colonic epithelial cells will increase colonic epithelial exposure and $R_{ox}$. Both EGF and its receptors are decreased in the elderly. There is also an increase in ulcerative colitis in people 60 and older. Thus, the measurement of levels of EGF and its receptors is a useful diagnostic indicator of $R_{ox}$.

Assays Related to Glutathione Levels Include:

1. Tests that directly or indirectly measure levels of the reduced form of glutathione (GSH) in blood, colonic tissue or feces. When GSH is decreased, hydrogen peroxide will go un-neutralized and will increase. Only the reduced form of glutathione can neutralize hydrogen peroxide.

2. Tests that directly or indirectly measure the oxidized form of glutathione in blood, colonic tissue or feces. Oxidized glutathione (GSSG) is produced after hydrogen peroxide is neutralized. If there is too much hydrogen peroxide to eliminate, GSSG will increase.

3. Tests that directly or indirectly measure glutathione reductase levels. Glutathione reductase is an enzyme necessary to convert oxidized glutathione (GSSG) to the reduced form (GSH). If the activity of this enzyme is decreased, then hydrogen peroxide will increase causing an increased $R_{ox}$.

4. Tests that directly or indirectly measure NADPH levels. NADPH is the critical reducing agent that donates electrons to (GSSG) so it can be regenerated back to GSH (reduced glutathione). If NADPH is decreased, then hydrogen peroxide will increase.

5. Tests that directly or indirectly measure G-6-PD (glucose-6-phosphate dehydrogenase), H-6-PD (hexose 6-phosphate dehydrogenase) and/or 6-PGD (6-phosphogluconate dehydrogenase activity. Almost all the NADPH needed to regenerate oxidized glutathione (GSSG) back to the useful reduced form (GSH) necessary to neutralize hydrogen peroxide is produced by one biochemical pathway, the phosphate pentose pathway (PPP) (formally known as the hexose monophosphate shunt). Within the PPP two dehydrogenase enzymes are exclusively responsible for the production of all the NADPH generated. These are G-6-PD (glucose-6-phosphate dehydrogenase, EC 1.1.1.49) and 6-PGD (6-phosphogluconate dehydrogenase, EC 1.1.1.44). Genetic deficiency of G-6-PD (the 'G' form) has been described and will cause hemolysis of red blood cells which lack a normally occurring back-up enzyme known as H-6-PD (hexose-6-phosphate dehydrogenase, the "H" form) present in other cells of the body. Presence of the both the G and H forms allows the PPP to produce a normal amount of NADPH providing there is normal activity of the second NADPH producing enzyme, 6-PGD. However, 6-PGD (6-phosphogluconate dehydrogenase) does not have an effective back up and can be present in a polymorphic form with decreased activity of up to 50%. This could theoretically decrease total colonic epithelial NADPH by as much as 25%. Decreased NADPH will allow hydrogen peroxide to increase elevating the $R_{ox}$ predisposing the colon to oxidative injury.

6. Tests that directly or indirectly measure butyrate levels. If colonic epithelial butyrate levels are low, then glutathione will be decreased. This will cause hydrogen peroxide to increase.

7. Tests that directly or indirectly measure the levels of glycine, cysteine and glutamic acid. If any of the three amino acids necessary for glutathione production (glycine, cysteine and glutamic acid) are low, then less GSH will be produced and hydrogen peroxide will increase.

Factors associated with increased and decreased risk of inflammatory bowel diseases have been identified. Factors that increase the risk of developing inflammatory bowel diseases include stress, alcohol consumption, diet and xenobiotic metabolism. Thus, the subject methods also include modification of patient behavior, either alone or in combination with the administration of a therapeutic composition of the invention.

Positive Risk Factors (Increased Risk of Induction):

Rectum: The greatest risk factor for ulcerative colitis is the presence of a rectum. Within this area of the colon a junction of physiological parameters converge to increase the potential for $H_2O_2$ generation and oxidative tissue damage (induction). Studies have shown that the reducing power (antioxidant capacity) and GSH synthetic rate of the rat intestine decreases distally, reaching its lowest level in distal colon when compared to the proximal small intestine (Blau, 1999). The reducing power of the human gastrointestinal tract likewise decreases from stomach to colon (Roediger and Babige, 1997). The reducing power of the human colon is significantly decreased when compared to the liver with levels of major anti-oxidant enzymes (catalase, superoxide dismutase and glutathione peroxidase) being 4, 8, and 40% of hepatic values respectively (Matthew et al., 1990). However, rectal epithelial cells have the same complement of enzymes, i.e., cytochrome oxidase, xanthine oxidase, etc., as the liver for use in metabolism of foreign substances including alcohol and xenobiotics (Roediger and Babige, 1997). One by-product of this metabolism is hydrogen peroxide that the rectal epithelium is ill equipped to deal with if produced in excess. Un-neutralized excess $H_2O_2$ may diffuse to the extracellular space and induce oxidative damage to the colonic epithelial barrier thereby increasing its permeability to luminal bacterial antigens. Any substance found in the body which, through its metabolism, can give rise to hydrogen peroxide in rectal epithelial cells is a positive risk factor for ulcerative colitis induction.

The bacterial concentration within the colon increases distally from $10^3$ cfu/gram of fecal material in the cecum to $10^{13}$ cfu/gram in the rectum. The greatly increased concentration of, predominantly, mucosal adherent anaerobic bacteria significantly increases the likelihood of antigenic exposure in the event of a barrier breakdown. Any condition which slows colonic fecal transport allows bacteria more time to multiply. This increase in intra luminal bacterial concentration is a positive risk factor for ulcerative colitis induction. High concentrations of bacteria also increase the likelihood of horizontal transmission of genetic material including antibiotic resistance and virulence factors.

Fecal material also generates a large amount of oxygen radicals, in part due to the high concentration of bacteria in addition to the fecal matrix and other luminal substances including xenobiotics, toxins and bile acids (Owen et al., 2000, Harris et al., 1992). The increased concentration of these radicals found in the rectum, a fecal reservoir, can also contribute to colonic barrier dissolution and epithelial oxidative damage. Therefore, any condition which increases colonic bacterial concentration or metabolism will increase the production of luminal oxygen radicals and is a positive risk factor for ulcerative colitis induction.

Rectal epithelial cells also possess an electron transport chain which may become a source of excess $H_2O_2$ if subjected to hypoxia and sudden re-oxygenation (Chuanyu and Jackson, 2002). During the time the rectum is housing feces and until they are expelled the rectal wall is subjected to lateral pressure which can compress delicate sub-mucosal blood vessels. During this time the rectal epithelial cells are exposed to a relative hypoxia which is suddenly followed by swift reperfusion as the fecal material is expelled. This process of hypoxia and re-oxygenation increases the activity of the electron transport chain resulting in increased production of hydrogen peroxide. Any condition that induces or increases constipation significantly magnifies this effect and is a risk factor for entering the induction phase of ulcerative colitis. Approximately 10 to 16% of ulcerative colitis patients have fecal stasis and investigators have observed that slow colonic transit may predispose to ulcerative proctitis (Allison and Vallance, 1991; Black et al., 1987).

Another contributing factor to the production of hydrogen peroxide during hypoxia and re-oxygenation is the effect of xanthine oxidase (Granger and Parks, 1983; Parks et al., 1984; Parks and Granger, 1986). Xanthine oxidase catalyzes the conversion of hypoxanthine to uric acid and in the process reduces molecular oxygen to hydrogen peroxide. During hypoxia xanthine oxidase activity is significantly reduced due to unavailability of oxygen needed as an electron accepting co-factor for the enzymatic conversion (oxidation) of hypoxanthine to uric acid. When oxygen is reintroduced an increased substrate load leads to increased hypoxanthine metabolism and hydrogen peroxide production. Constipation and straining during defecation, by increasing colonic intraluminal pressure, will enhance the effect of hypoxia/reoxygenation upon the xanthine oxidase enzyme system, increasing its activity and output of $H_2O_2$ which increases the risk of entering the induction phase of ulcerative colitis. Allopurinol, an inhibitor of xanthine oxidase, can decrease the production of $H_2O_2$ by colonic epithelial cells under these conditions.

Stress: Stress has several effects on the gastrointestinal tract. Sleep deprivation stress increases the bacterial translocation through the intestinal epithelium (Everson and Toth, 2000). Stress also activates intestinal mast cells with subsequent increase in permeability due to modulation of mucosal barrier function (Soderholm et al., 2002). Psychological and physical stress are reported to cause enterocyte physiology abnormalities, goblet cell dysfunction, increased mucosal bacterial adherence and increased intestinal permeability and secretion (Soderholm and Perdue, 2001).

Stress also increases the amount of circulating biogenic amines (catecholamines), such as serotonin, epinephrine, nor-epinephrine and dopamine (Lechin et al., 1996). Monoamine oxidase (EC#1.4.3.4), an enzyme present on the outer surface of mitochondria, catalyzes the oxidative deamination of both xenobiotic amines as well as the aforementioned catecholamine stress hormones and in the process reduces molecular oxygen to hydrogen peroxide (Cadenas and Davies, 2000). The reaction catalyzed is: $RCH_2+H_2O+O_2 \rightarrow RCHO+NH_3+H_2O_2$ Therefore, any condition of sustained stress can increase the concentration of circulating endogenous catecholamines and boost production of hydrogen peroxide by rectal epithelial cells. This is a positive risk factor for entering the induction phase of ulcerative colitis. Likewise, measures aimed at reducing circulating endogenous catecholamine with reduced $H_2O_2$ production by colonic epithelial cells and decrease the risk of rectal epithelial barrier damage. Clonidine, a central alpha 2 agonist has been used successfully in this regard. Thus, the methods of the present invention also contemplate modification of patient behavior and/or physiology to reduce stress on the patient and/or the effects of stress on the patient.

Xenobiotics: The majority of oxidation reactions of drugs and other xenobiotics are carried out by Cytochrome enzymes. One study reports 56% of over 300 drugs tested are metabolized via the Cytochrome p450 (CYP) family of oxygenase enzymes present in the endoplasmic reticulum (Bertz and Granneman, 1997). CYP is mostly found in the liver but is also present in the intestine. A typical CYP catalyzed reaction is:

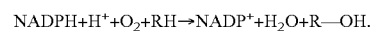

$NADPH+H^++O_2+RH \rightarrow NADP^++H_2O+R-OH.$

This reaction consumes NADPH which is also used in regeneration of reduced glutathione. Glutathione is the major antioxidant involved in the neutralization of intracellular hydrogen peroxide. Due to the extensive inter-individual polymorphism observed in the CYP enzyme system certain individuals may have greater activity then others and can metabolize xenobiotics at a faster rate consuming more NADPH in the process. These individuals are called fast metabolizers. Fast metabolizers are at a greater risk of entering the induction phase of ulcerative colitis when exposed to certain drugs.

Alcohol: After ingestion, alcohol is distributed to all cells of the body including the rectal epithelial cells. Alcohol is enzymatically converted to acetaldehyde by alcohol dehydrogenase. The acetaldehyde is enzymatically converted to acetic acid by aldehyde dehydrogenase. Both of these cytosolic enzymes utilize $NAD^+$ to oxidize their respective substrates and generate NADH that normally serves as an electron donor to the electron transport chain. The increased availability of NADH can activate the electron transport chain and generate excess hydrogen peroxide (Hoek et al., 2002; Shannon, 1999).

Alcohol can also be metabolized in the endoplasmic reticulum by cytochrome p450 2E1 which depletes NADPH needed for glutathione regeneration. Alcohol can therefore generate $H_2O_2$ and decrease production of glutathione needed for neutralization of hydrogen peroxide. High $H_2O_2$ and depleted glutathione increases the risk of entering the induction phase of ulcerative colitis.

Alcohol inhibits glutathione peroxidase; a crucial enzyme that neutralizes $H_2O_2$, and depletes mitochondrial glutathione (Hoek et al., 2002). Glutathione is not synthesized within mitochondria and must be transported from the cytoplasm into the mitochondria through the mitochondrial membranes. Alcohol interferes with the active transport of glutathione into the mitochondria (Maher, 1997). This leads to mitochondrial depletion of glutathione and $H_2O_2$ accumulation. Depleted glutathione and increased $H_2O_2$ levels enhance the risk of entering the induction phase of ulcerative colitis. Thus, the methods of the invention contemplate modification of patient intake of alcohol and alcoholic beverages.

Constipation:

Based on surveys of bowel habits constipation occurs in up to 20% of the population (Drossman et al., 1999; Everhart et al., 1987). Constipation is reported to occur in 27% of patients with ulcerative colitis (Rao, 1988). Constipation is a common but often an overlooked condition that can have a serious exacerbating impact on almost any disease especially ulcerative colitis. At the 13th International Congress of Gastroenterology in Rome, Italy in 1988 a group of physicians defined criteria to more accurately diagnose several different functional bowel disorders including constipation. Known as the "Rome Criteria," this set of guidelines outlines symptoms and applies parameters such as frequency and duration in order to make possible a more accurate and standardized diagnosis of constipation. In 1999, a second set of updated guidelines, Rome II, was published (Drossman et al., 2000). The Rome II definition of functional constipation consists of the following parameters:

At least 12 weeks, which need not be consecutive, in the preceding 12 months of two or more of:
1. Straining in over 25% of defecations;
2. Lumpy or hard stools in over 25% of defecations;
3. Sensation of incomplete evacuation in over 25% of defecations;
4. Sensation of anorectal obstruction or blockage in over 25% of defecations;
5. Manual maneuvers to facilitate over then 25% of defecations (e.g. digital evacuation, support of pelvic floor) and/or
6. Less than 3 defecations per week.

Loose stools are not present, and there are insufficient criteria for IBS.

As stated above, constipation is a significant exacerbating factor for ulcerative colitis. Twenty seven percent of individuals with ulcerative colitis have coexisting constipation. Constipation can contribute to the development of the induction phase of ulcerative colitis in several ways. Increased colonic transit time favors bacterial overgrowth which increases the antigenic stimulus once the colonic epithelial barrier is disrupted. Constipation also allows for greater contact time between fecal generated oxygen radicals and the colonic mucosa which may deplete the already low antioxidant stores of the epithelial lining.

Large accumulations of un-expelled rectal fecal material may increase lateral pressure on the rectal mucosa and collapse delicate sub mucosal capillary beds predisposing to a reoccurring perfusion-reperfusion oxidative insult to the colonic epithelium. Constipation will significantly decrease the amount of butyrate reaching the rectal epithelium due to proximal colonic absorption and further exacerbate oxidative injury due to glutathione depletion. Thus, the methods of the invention contemplate treatments and/or modification of patient diet to relieve and/or minimize constipation and to provide for regular bowel movement.

Diet:

Butyrate: Dietary factors can contribute to induction of ulcerative colitis. The preferred energy source for colonic epithelial cells is a four chain fatty acid known as butyrate. It originates from two dietary sources. Most butyrate is derived from colonic bacterial fermentation of unabsorbed dietary fiber and is the single largest metabolite of dietary fiber. The second significant source dietary source is from butter which contains 3% butyrate. Butyrate is a short chain fatty acid (SCFA) and is produced along with two other SCFAs (acetate and propionate) as a result of bacterial fermentation of dietary fiber (Topping and Clifton, 2001).

Ninety-five percent of SCFAs are produced and absorbed in the colon. Fermentation and SCFA production are high in the proximal large bowel. During passage of the fecal stream, fermentation declines secondary to depletion of available substrate. By the time the fecal mass reaches the rectum less than 5% of bacterially derived SCFA are available for colonocyte uptake. Proximal colonic absorption is responsible for this significant decline.

SCFAs are the metabolized rapidly by colonocytes and are the major respiratory fuels supplying 70% of colonocytes energy needs (Topping and Clifton, 2001). Colonocytes prefer to use butyrate even when competing substrates such as glucose, glutamine and other SCFAs are present.

The distal colon and rectum are the regions of the large intestine with the most limited supply and slowest absorption of butyrate and is the site of most pathology including ulcerative colitis. When the amount of butyrate is insufficient to meet the energy needs of colonic epithelial cells an alternate source of energy is utilized and the colonic epithelial cells will switch to glucose and the amino acid glutamine.

Glutamine is synthesized from glutamic acid, its immediate precursor. Glutamic acid is also used to synthesize glutathione which is needed to neutralize hydrogen peroxide. If too much glutamic acid is diverted to the formation of glutamine as an energy source then less is available for colonic epithelial glutathione synthesis. This can result in a diminished intracellular glutathione concentration with a corresponding increase in hydrogen peroxide. Therefore, the lack of dietary fiber is a positive risk factor for entering the induction phase of ulcerative colitis.

On a wider scale, 90% of butyrate and other SCFAs are metabolized via beta-oxidation within mitochondria of colonocytes (10% within peroxisomes). Conditions that interfere with beta-oxidation will force the utilization of an alternate energy source such as glutamine. Beta-oxidation is decreased when sufficient substrate (i.e., butyrate) is unavailable to the rectal epithelial cells. Inadequate rectal luminal butyrate can occur with inadequate ingestion of fermentable dietary fiber or increased colonic transit time (constipation). Butyrate cannot be detected in feces at whole gut transit time exceeding 50 hours (Topping and Clifton, 2001).

Roediger and Nance report the induction of ulcerative colitis in rats after rectal instillation of a specific inhibitor of beta-oxidation (Roedinger, 1986). The authors conclude that "a suitable inhibitor of beta-oxidation would have unimpeded entry into mitochondria of colonic epithelial cells." Hydrogen peroxide is permeable through biomembranes including the cell membrane and both the inner and outer mitochondrial membranes. Hydrogen peroxide has been shown to inhibit the beta-oxidation enzyme system of enzymes (Gulati et al., 1993). $H_2O_2$ produced as a consequence of neutrophil activation within colonic mucosa during active ulcerative colitis is therefore capable of diffusing back into colonic epithelial cells resulting in oxidative damage to intracellular proteins including enzymes of beta-oxidation. This would explain the abnormalities of butyrate metabolism during active ulcerative colitis which resolve during remission. Thus, the methods of the invention also contemplate modification of patient diet to provide for sufficient glutathione in colonic epithelial cells including, for example, providing for sufficient dietary fiber in a patient being treated or at risk for developing an inflammatory bowel disorder.

Fat: High intakes of mono and poly unsaturated fat may enhance the risk of developing ulcerative colitis. The concentrations of lipid peroxides found in common foods cooked in oils or fats (hamburger, French fries) can produce mucosal oxidative stress and redox imbalance when in contact with intestinal mucosa (Aw, 1999). Rats fed high fat diets had seven fold greater intestinal production of superoxide when compared to controls. Intestinal lipid peroxidation and hydroxyl radical was increased 3.5 fold. Intestinal mucosal DNA fragmentation was increased 2.4 times (Bagchi et al., 1998). Oxidative DNA damage suggests that there is a high cytoplasmic oxidative environment. The presence of high fat intake is a positive risk factor for entering the induction phase of ulcerative colitis. Thus, the methods of the invention also contemplate modification of patient diet to decrease intake of fat.

Spices: Spicy food was found to produce similar oxidative stress on intestinal mucosa as a high fat diet. Intestinal mucosal hydroxyl radical production in rats fed spicy foods was found to be 4.8 times normal, even greater than rats fed a high fat diet (Bagchi et al., 1998). Spicy food intake should be considered a positive risk factor for entering the induction phase of ulcerative colitis.

Meat: A diet high in red meat (beef) has been reported to increase the intestinal Bacteroides population (Maier et al., 1974). This effect persisted for several weeks after terminating the high beef diet and while on a normal diet regimen. Bacteroides species have been implicated as the inciting antigenic agent in ulcerative colitis (above).

Vitamins and Minerals:

Folic Acid:

Methylenetetrahydrofolate reductase (MTHFR) (EC 1.5.1.20) is one of the main regulatory enzymes of homocysteine metabolism and plays a major role in the metabolism of folates (Friedman et al., 1999; Goyette et al., 1998). MTHFR is a cytoplasmic enzyme that catalyzes the NADPH-linked reduction of methylene-tetrahydrofolate to methyl-tetrahydrofolate. Methyl-tetrahydrofolate serves as the methyl donor for the methylation of homocysteine. Mutations in the gene coding for MTHFR have been found. This genetic mutation results in a cytosine to thymine transition at base position 677 which converts alanine to valine at amino acid position 222 (A222V). The polymorphic MTHFR enzyme (C677T) has significantly less activity than normal (35-50% of normal) resulting in an elevation of serum homocysteine levels (Goyette et al., 1998).

Molloy et al. report that 17.5% of individuals with ulcerative colitis are homozygous for the C677T variant of the MTHFR gene versus 7.3% of controls (Molloy et al., 1999).

Elevated homocysteine will increase hydrogen peroxide production by several mechanisms. $H_2O_2$ is generated during the oxidation of homocysteine to homocystine (Friedman et al., 1999; Upchurch, et al., 1997). Homocysteine also increases superoxide dismutase (SOD) levels (Wilcken et al., 2000). SOD catalyzes the conversion of superoxide anion to hydrogen peroxide. Increased activity of this enzyme will result in greater $H_2O_2$ generation. Homocysteine has been reported to inhibit glutathione peroxidase (GPx) activity (Upchurch et al., 1997) by 10 fold (Outinen et al., 1999). GPx is an essential enzyme system which neutralizes intracellular $H_2O_2$. Inactivation of GPx will increase $H_2O_2$ levels and inhibition of GPx was shown to occur at physiologic (9 micromol/L) concentrations of free homocysteine (Chen, 2000).

Biogeographically, the worldwide distribution of the C677T polymorphic variant also points to a role for the deleterious effects of this modified enzyme in the development of ulcerative colitis. The T allele was found to have a frequency of 40% in North America but was very low in Africa and Asia (The Metabolic and Molecular Basis of Inherited Disease, 2001, 8th ed., Chapter 155, Vol. 3, pp. 3897-3993). This parallels the incidence of ulcerative colitis which is more common in North America and less common in Asia and Africa (Whelan, 1990; Farrokhar et al., 2001).

The ethnic distribution of C677T also suggests a role in ulcerative colitis. Rady et al. found that the rate of C677T among Ashkenazi Jewish alleles was 47.7% compared to 28.7% among the non-Jewish population (Rady et al., 1999). Ulcerative colitis is also reported to be more common in the Jewish population (Roth et al., 1989; Karling, 2000).

In other words, this variant MTHFR enzyme can increase colonic epithelial intracellular hydrogen peroxide by increasing SOD levels, inactivating glutathione peroxidase, inhibition of glutathione synthesis and increasing production of homocysteine which generates $H_2O_2$ during its oxidation. The physiological effects of the C677T variant of MTHFR may contribute enough oxidative stress in the form of additional $H_2O_2$ to tip the balance towards entering the induction process of ulcerative colitis.

The oxidative phenotype associated with C677T may have enough penetrance to predispose certain ethic groups and geographical populations to manifest a higher incidence of ulcerative colitis. Therefore, the presence of this polymorphic MTHFR should be considered a positive risk factor for entering the induction phase of ulcerative colitis.

Additionally, the lack of normal folate metabolism may decrease availability of the essential amino acid methionine which is a precursor of the amino acid cysteine. Cysteine is one of the three peptides needed to synthesize glutathione. Glycine, another component amino acid of glutathione, also requires folate for its synthesis. Folate deficiency or inhibition of folate metabolism may therefore directly interfere with adequate production of glutathione and contribute to increased intracellular oxidative stress via increased hydrogen peroxide levels.

Low serum level of multiple vitamins, including folate has been reported in association with ulcerative colitis (Fernandez-Banares et al., 1989; Elsborg and Larsen, 1979; Koutroubakis et al., 2000). This has been attributed to the effects of inadequate diet, intestinal malabsorption or drug induced (Elsborg and Larsen, 1979). Co-existing folate deficiency would tend to exacerbate the oxidative effects of MTHFR polymorphism as indicated above. In monkeys, experimentally induced folate deficiency leads to colonic ulcerations (Duncan, 1964).

Vitamin B-6:

High intakes of pyridoxine (vitamin B-6) have been reported to enhance the risk of ulcerative colitis (Geerling et al., 2000). Vitamin B-6 is oxidized in the body by Pyridoxine 4-oxidase to pyridoxal via the reaction: Pyridoxine+ $O_2 \rightarrow$ pyridoxal+$H_2O_2$. This mainly occurs in the liver but can occur in other places such as the gastrointestinal tract. A toxic by-product of this reaction is hydrogen peroxide. Therefore, excessive pyridoxine is a positive risk factor for entering the initiation phase of ulcerative colitis.

Iron and Copper:

A single electron reduction is the only type of reaction which leads to the formation of hydroxyl radical from hydrogen peroxide. The electron donating agent may be an electron donating radical such as superoxide ($O_2^-\cdot$) or a biologically significant redox transition metal such as iron or copper (Eberhardt, 2001). These one electron reduction reactions of $H_2O_2$ and other peroxides represent the most important radical forming reactions in biological systems and are responsible for most hydroxyl generation in human cells.

$Fe^{+2} + H_2O_2 \rightarrow Fe^{+3} + HO^- + HO\cdot$ Fenton reaction $O_2^{-}\cdot + H_2O_2 \rightarrow O_2 + HO^- + HO\cdot$ Haber-Weiss reaction Iron can act as an intermediate and facilitate the transfer of a single electron from superoxide to hydrogen peroxide. The presence of iron will accelerate the generation of hydroxyl radical from hydrogen peroxide via the iron catalyzed Haber-Weiss reaction (Eberhardt, 2001; Graf et al., 1984).

$O_2^{-}\cdot + Fe^{+3} \rightarrow O_2 + Fe^{+2}$ Ferric Iron ($Fe^{+3}$) catalyzed $Fe^{+2} + H_2O_2 \rightarrow Fe^{+3} + HO^- + HO\cdot$ Haber-Weiss reaction.

Within cells, iron is coupled to biological macromolecules such as proteins and DNA. The formation of hydroxyl radical will therefore take place in close contact with these molecules. Since the hydroxyl radical is highly reactive, the damage caused by this very powerful oxidizing agent occurs at the site of formation (Eberhardt, 2001). This rapid site specific target oxidation prevents radical scavengers from interfering with this reaction and greatly magnifies the damaging effects of the $H_2O_2/HO\cdot$ system. Even in the absence of readily available reactive surface iron atoms, superoxide can induce the release of iron from storage proteins such as ferritin and enzymes. This released iron is then able to generate hydroxyl by reacting with hydrogen peroxide (Keyer and Imlay, 1996; Liochev and Fridovich, 1999). Thus, within biological systems, superoxide is able to provide a steady supply of its own iron catalyst needed to perpetuate the production of hydroxyl from hydrogen peroxide. Conversely, iron overload can damage tissues even when superoxide concentrations are minimal, suggesting that other reducing agents besides $O_2^{-}\cdot$ can supply the electrons necessary to free iron when it redox-cycles with $H_2O_2$ (Keyer and Imlay, 1996).

In accordance with these observations, iron supplementation has been reported to damage the GI tract via the formation of oxygen radicals and to worsen experimentally induced colitis in laboratory animals (Srigiridhar et al., 2001; Reifen et al., 2000). Human ulcerative colitis has also been reported as a consequence of oral ferrous sulfate treatment for anemia (Kawai et al., 1992). Conversely, iron chelation has been reported to reduce the production of reactive oxygen species in patients with ulcerative colitis (Millar et al., 2000).

Excessive iron intake in the form of supplements or red meats (i.e., beef), therefore, may enhance the production of (GI barrier) damaging hydroxyl radical and facilitate the transition from the induction phase to the propagation phase of ulcerative colitis. Excessive iron is therefore a risk factor for entering the propagation phase of ulcerative colitis.

Copper is reportedly present in higher than normal amounts in active and quiescent human ulcerative colitis (Dalekos et al., 1998; Ringstad et al., 1993) and may be a contributing factor in the formation of hydroxyl radical. Human ulcerative colitis has been reported in association with and subsequent to the development of Wilson's disease in which abnormally high copper levels are present in body tissues (Torisu, 2002). As with iron, excessive copper can accelerate the reduction of $H_2O_2$ and increase the generation of hydroxyl radical. Excessive copper can therefore be considered a risk factor entering the propagation phase of ulcerative colitis.

Vitamin C:

Vitamin C (ascorbic acid) is an antioxidant that reacts with oxygen radicals. However, serial oxidations of the ascorbyl radical can generate hydrogen peroxide that gives rise to the hydroxyl radical in the presence of iron or copper (Eberhardt, 2001). Combined ascorbic acid and mineral supplements can be a positive risk factor for entering the induction phase of ulcerative colitis. Ascorbate can also be oxidized by L-ascorbate oxidase which generates hydrogen peroxide as a by product. Excessive intake of vitamin C of itself may be a contributing risk factor induction in ulcerative colitis.

Vitamin B-1:

Thiamine (Vitamin B-1) can be metabolized by Thiamine oxidase which generates $H_2O_2$. Excess thiamine can be a contributing risk factor for entering the induction phase of ulcerative colitis.

Artificial Sweeteners:

Artificial sweeteners such as Sorbitol and Xylitol are oxidized by Xylitol oxidase which generates hydrogen peroxide. If consumed in large amounts can be a risk factor for induction in ulcerative colitis.

Aspartame is an artificial sweetener used extensively in many products including soft drinks and baking goods. It is commonly seen in a small blue packet along with sugar and saccharine in many restaurants. Aspartame is a dipeptide composed of two amino acids, L-phenylalanine as the methyl ester (Phe) and L-aspartic acid (Asp). About 10 percent by weight of aspartame is released as methanol. Methanol can be metabolized by methanol oxidase to formaldehyde and $H_2O_2$. Aspartic acid is metabolized by aspartic oxidase with the release of $H_2O_2$. Phenylalanine is metabolized by amino acid oxidase with the subsequent release of $H_2O_2$. The amount of oxidative stress caused by aspartame depends on the amount ingested. Since this product is so ubiquitous its contribution to colonic epithelial hydrogen peroxide may exceed that from general protein amino acid intake and may be a risk factor for induction in susceptible individuals.

Monosodium Glutamate:

Monosodium glutamate (MSG) is the sodium salt of the amino acid glutamic acid. It is used in high concentrations as a flavor enhancer. Glutamic acid is metabolized by glutamate oxidase and hydrogen peroxide is released as a by-product of this reaction. The oxidative load of MSG will depend on the amount consumed. Susceptible individuals that consume a large amount of MSG may be at risk for entering the induction phase of ulcerative colitis.

Thus, the methods of the invention also contemplate modification of the intake of and levels of vitamins, artificial sweeteners, and food additives in a patient.

Negative Risk Factors (Decrease Risk of Induction):

Certain factors have been found to decrease the risk of developing ulcerative colitis. Chief among them is the association of cigarette smoking with a decreased incidence of developing ulcerative colitis (Abraham et al., 2003; Odes, 2001). Some investigators have labeled ulcerative colitis a disease of non-smokers (Madretsma, 1996). The risk of developing ulcerative colitis is greatest among individuals who have recently quit smoking followed by non-smokers (Farrell and Peppercorn, 2002).

Tar products in tobacco smoke have been shown to inhibit the electron transport chain. Studies quantifying the effect of cigarette tar on mitochondrial electron transport activity report an 82% inhibition rate on whole chain respiration (Pryor et al., 1992). In this study nicotine had no effect on electron transport activity. ETC inhibition will reduce mitochondrial hydrogen peroxide generation. Cigarette smokers have also been reported to have reduced monoamine oxidase activity (Fowler et al., 2003). MAO, located on the mitochondrial outer membrane, is the main enzyme responsible for endogenous catecholamine metabolism. Inhibition of this enzyme decreases enzymatic oxidation of catecholamines and the generation of hydrogen peroxide which is a by-product of this reaction. Extracts of cigarette tar are reported to inhibit a number of P450 enzyme systems (Van Fleet et al., 2000). Hydrogen peroxide is a by-product of P450 metabolism and inhibition of these enzymes can lower $H_2O_2$ generation.

Cigarette smoke extract has also been reported to inhibit the production of cytokines, including TNF-alpha, by greater than 90%. (Ouyang et al., 2000). Cytokines are an integral component of the inflammatory response in ulcerative colitis and their reduction may confer protection.

Thus, smoking may confer protection by inhibiting $H_2O_2$ production and preventing the induction phase of ulcerative colitis. However, during the time the ETC is inhibited by smoking, reducing equivalents, the substrate for $H_2O_2$ production, have been accumulating within mitochondria of all cells of the body including colonic epithelial cells. Inhibition of the electron transport chain also causes up-regulation of ETC associated enzymes in an attempt at overcoming the blockade. During the time of ETC inhibition glutathione production may also be down regulated since the cell does not have use for high levels of antioxidants when $H_2O_2$ production is low.

When an individual suddenly stops smoking this inhibition is abruptly removed resulting in greater ETC activity fueled by increased substrate and enzymatic activity. This also results in extra hydrogen peroxide being produced which, in susceptible individuals, may overwhelm the available glutathione within the colonic epithelial cells and increase the risk of induction.

Based on ETC inhibition, the risk of induction would be expected to be lowest in active smokers. Smokers that have recently quit smoking would be at highest risk since they are producing the most $H_2O_2$ Non-smokers would have the lowest risk. This mirrors the statistical risk of smoking as it relates to ulcerative colitis.

Smoking cessation during active ulcerative colitis would therefore be expected to exacerbate the condition. An increase in severity of ulcerative colitis has been reported in patients who stopped smoking during active ulcerative colitis (Beaugerie et al., 2001).

Nicotine is a parasympathomimetic and exerts its effect on the GI tract largely by stimulation of the parasympathetic ganglia. Its effect is to generally increase tone and contractility (National Academy of Sciences, 2001). The nicotine in cigarette smoke enhances intestinal peristaltic activity which tends to increase the fecal stream and prevent fecal stasis which can increase colonic bacterial and epithelial oxidant stress loads. Abrupt cessation of this adjuvant to colonic peristaltic activity would tend to favor stasis of colonic contents and promote constipation which is a risk factor for the development of ulcerative colitis (see constipation above). Thus, the methods of the invention contemplate regulated, progressive cessation of smoking in a patient.

Co-Morbid Conditions:

Ulcerative colitis has been associated with hyperthyroidism. In one case report two patients developed ulcerative colitis while being followed for hyperthyroidism (Modebe, 1986). One of these patients had a second exacerbation of ulcerative colitis which could not be controlled until it was discovered that she was thyrotoxic. The ulcerative colitis only responded to therapy after controlling the hyperthyroidism.

Another study compared the frequency of thyroid disease between 300 patients with documented ulcerative colitis and 600-age and sex matched normal controls (Jarnerot et al., 1975). A history of thyrotoxicosis was obtained in 3.7% of the ulcerative colitis patients compared with 0.8% of controls. Seventy percent of the ulcerative colitis patients developed hyperthyroidism prior to developing ulcerative colitis. Although ulcerative colitis patients can subsequently develop hyperthyroidism it is unlikely that a subclinical hyperthyroid state will be uncovered before the patient seeks treatment for ulcerative colitis and therefore the number of ulcerative colitis patients with preceding hyperthyroidism may be underestimated.

The colon and the thyroid gland have dissimilar embryological origins arguing against a common cross-reactive antigenic stimulus for the development of an auto-immune pathogenesis as an etiology in both diseases.

Thyroid hormone is known to raise the metabolic rate. It accomplishes this by increasing the activity of the mitochondrial electron transport chain (Venditti et al., 2003; Goglia et al., 2002; Venditti et al., 1997). Under the influence of excess thyroid hormone greater amounts of hydrogen peroxide are generated and released via accelerated mitochondrial ETC activity (Venditti et al., 2003).

Thus, increased ETC activity results in higher intracellular $H_2O_2$ production in all cells of the body including colonic tissue. Under appropriate conditions this can result in colonic epithelium entering the induction phase of ulcerative colitis when excess un-neutralized $H_2O_2$ diffuses out of the colonic epithelial cell.

Conversely, chemically induced hypothyroidism is reported to significantly attenuate animal models of experimental colitis (Isman et al., 2003; Maaravi et al., 1997). This suggests that $H_2O_2$ constitutively produced in the euthyroid state presents a major oxidant load to the cell and results in the consumption of significant amounts of intracellular glutathione.

Thus, the methods of the invention contemplate the use of compositions and methods to control thyroid hormone levels in a patient.

Genetic Factors:

Ulcerative colitis has an approximate 10% concordancy rate between mono-zygotic twins (Farrell and Peppercorn, 2002). This suggests that environmental factors are diverse and very influential in the development of the disease. The lack of an identifiable genotype suggests that genetic factors are multiple (not singular) and with insufficient penetrance to elicit the disease on their own.

In other words, environmental exposure of synergistic factors each of which is beneath the threshold to elicit a recognizable pathogenic response on their own may be acting in concert with several genetic factors of weak penetrance which overlap in only 10 percent of monozygotic twins in order for ulcerative colitis to occur.

Genetic research performed by Cho et al. uncovered the existence of a pathophysiologically crucial IBD susceptibility gene (1p36) located on the small arm of human chromosome 1 (Cho et al., 2000; Cho et al., 1998). This genetic locus codes for two enzymes that are able to influence the intracellular redox environment at a fundamental level.

The first enzyme, Methylenetetrahydrofolate Reductase (MTHFR, EC 1.5.1.20), has several polymorphic variant phenotypes which interfere with normal folate metabolism (above). It is located at 1p36.3. It is present in about twenty percent of individuals with ulcerative colitis. This polymorphic enzyme causes elevation in serum homocysteine and a decrease in methionine and glycine. This epistatic effect can inhibit glutathione peroxidase function and interfere with glutathione synthesis, both of which are essential for detoxification of hydrogen peroxide. This results in higher than normal intracellular $H_2O_2$ and increased risk of ulcerative colitis induction (above). Persons with mutant or defective MTHFR might be treated prophylactically with folate and trimethylglycine.

A second enzyme located at this locus (1p36.3) is 6-Phosphogluconate dehydrogenase (PGD) (EC 1.1.1.44). PGD is the second dehydrogenase enzyme in the pentose phosphate pathway (hexose monophosphate shunt) which is responsible for production of NADPH. PGD catalyzes the conversion of 6-phosophogluconate to ribulose-5-phosphate generating two molecules of NADPH. NADPH is crucial for the reduction of glutathione disulfide (GSSG) back to reduced glutathione (GSH) in order to neutralize the continuous production of hydrogen peroxide being generated within the cell. The pentose phosphate pathway is the major source of reducing equivalent (NADPH) that allows $H_2O_2$ generating systems, such as the ATP producing electron transport chain and most oxidase enzymes, to function. Without NADPH to regenerate reduced glutathione, intracellular enzymes would suffer irreversible oxidative damage from excess hydrogen peroxide and cellular function would cease within minutes as apoptosis is triggered.

PGD exists in several polymorphic forms with decreased activity ranging from 22 to 79% of normal (Davidson, 1967; Parr, 1966; Parr, 1967; Dern et al., 1966; Nelson, 1982). Decreased levels of glutathione have been reported as a result of a PGD polymorphic enzyme (Capari, 2001). This suggests that normal activity of both NADPH producing enzymes in the pentose phosphate pathway is necessary for normal glutathione levels. PGD activity can also be lowered by exogenous factors such as antibiotics, dietary fat and the ageing process (Cifci, 2002; Tomlinson, 1998; Gordillo, 1991).

Polymorphic variants of PGD can decrease the amount of NADPH being generated. Under the appropriate conditions, individuals with this genetic polymorphism may then be at greater risk for $H_2O_2$ accumulation within the cell and higher risk for ulcerative colitis induction. Compromised PGD activity may, therefore, contribute to the ulcerative colitis induction process in predisposed individuals.

Cytochrome p450 oxygenase is a part of a family of about 50 genetically distinct enzyme systems that metabolize xenobiotics. This enzyme utilizes NADPH as an electron donor in order to metabolize drugs and toxins that enter the body. As mentioned above NADPH is also needed to regenerate reduced glutathione. Therefore fast metabolizers of any specific drug will consume more NADPH when exposed to that drug. The diversion of NADPH from Glutathione regeneration to drug detoxification can increase the intracellular concentration of hydrogen peroxide and likewise the risk of ulcerative colitis induction. P450 enzymes also generate $H_2O_2$ during metabolism of xenobiotics further increasing the oxidative load.

Studies of normal appearing colonic mucosa have reported significant inter-individual variation of enzymes involved in glutathione synthesis and metabolism (Batist et al., 1988). Variation between individuals was considerable at 8 fold for glutathione-S-transferase, 10 fold for glutathione peroxidase, 16 fold for glutathione levels, 14 fold for gamma-glutamyl-transpeptidase and 5 fold for gamma-glutamylcysteine synthetase. These large enzyme variations directly or indirectly affect intracellular glutathione concentrations which itself shows a 16 fold variation between individuals.

Ethnic variation and enzymopathies has also been reported for phosphogluconate dehydrogenase (EC: 1.1.1.44), glutathione peroxidase (EC 1.11.1.19), glutathione reductase (EC 1.6.4.2), gamma-glutamylcysteine synthetase (EC 6.3.2.2), and glutathione synthetase (EC 6.3.2.3) (Scriver et al., 2001; Larsson and Anderson, 2001; Buetler and Matsumoto, 1975).

Genetic factors affecting colonic glutathione concentrations are numerous. Factors affecting the synthesis, reductive regeneration, or phase II bio-conjugation of glutathione can increase intracellular $H_2O_2$. Individually no single factor appears to be able to alter the redox balance to the point of excessive intracellular $H_2O_2$ accumulation. However, in the face of a confluence of these genetic factors and the appropriate environmental conditions the colonic epithelium's ability to neutralize intracellularly generated hydrogen peroxide may be compromised and the tissue can enter the induction phase of ulcerative colitis.

Thus, the methods of the invention also contemplate genetic screening of an individual and modification, as necessary, of lifestyle and/or institution of treatment regimens based on results of the screening.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

EXAMPLE 1

Treatment of Patient During Induction Phase

It has been discovered that ulcerative colitis, like many other diseases can be prevented if it is recognized during the induction phase. Recognition of the induction process is difficult since there are little or no symptoms or signs pointing to the colon as the source of the problem and the colon is histologically and macroscopically normal. Recognition at this stage requires a high index of suspicion coupled with some knowledge of the extra intestinal manifestations, xenobiotic associations, family and genetic history, ulcerative colitis epidemiological data and life style history.

A p-anca antibody at this time may be positive if the colonic epithelial barrier has been rendered sufficiently permeable to allow prolonged contact between the immune system and bacterial antigens in the colon. The p-anca antibody has been shown to be directed against a surface antigen of *B. Vulgatus* and is an indication of colonic barrier breach with subsequent immune activation. Evidence of increased colonic epithelial turnover may be found in fecal samples since $H_2O_2$ can induce epithelial proliferation. If a colonoscopy should be performed additional evidence of epithelial cell proliferation may be seen such as melanosis coli (Pardi et al., 1998). Immunological staining of colonic biopsies may reveal altered tight junction proteins such as cadherin and basement membrane abnormalities. In vivo conductance studies, if this were possible, would show increased permeability in macroscopically normal colonic tissue.

In patients that are determined to be in the induction phase, measures can be undertaken to implement lifestyle changes in order to reduce the oxidative stress on the colon. All xenobiotics and alcohol should be terminated. Smoking should be discontinued gradually rather than via a complete cessation, i.e., the patient should avoid going "cold turkey" when trying to stop smoking. Constipation should be corrected. Fast food should be eliminated and a diet high in antioxidants (vegetables and fruit), fiber, and good quality protein should be instituted. Stress reduction should be instituted with counseling if necessary.

EXAMPLE 2

Treatment of Patient During Propagation Phase

Currently, individuals are almost never recognized during the induction phase and only seek medical help because of rectal bleeding when the propagation phase has already developed. A colonic neutrophilic inflammatory reaction into the colonic mucosa cannot be reversed with the same measures used during the induction phase, although it is prudent to institute them in order to prevent re-induction after reversal of the inflammatory reaction has been accomplished.

Treatment of colonic inflammation during the propagation phase comprises one or more of the following:

1. Neutralization of colonic hydrogen peroxide.
2. Reduction of neutrophilic stimulation by colonic bacteria.
3. Termination of colonic epithelial cell lipid peroxidation.
4. Reduction of colonic mucosal permeability.

Neutralization of hydrogen peroxide is critical in order to terminate continued tissue damage. This can be accomplished, for example, with rectal instillation of sodium thiosulfate that will neutralize hydrogen peroxide to water and non-reactive sulfate products.

The stimulatory effect of colonic bacteria, mainly anaerobic Bacteroides, on neutrophils can be mitigated with bismuth subgallate which prevents bacterial adherence to the colonic epithelium and is bactericidal.

Termination of colonic epithelial lipid peroxidation can be achieved with d-alpha tocopherol (vitamin E) as the acetate or the succinate. This also adds viscosity to the solution which creates a steric hindrance to prevent cytokines and radicals from interacting with their target tissue.

Finally, cromolyn sodium can block colonic mast cells and decrease colonic permeability to luminal antigens.

This therapy can be administered as a retention enema once daily.

Oral therapy with Clonidine to reduce the oxidative effects of endogenous catecholamines secondary to stress can also be instituted. Pentoxyfylline has anti-inflammatory activity and may function as a purinergic agonist via an adenosine receptor on the surface of the infiltrating neutrophil which can inhibit NADPH oxidase and apoptosis. This oral therapy can be continued, along with lifestyle changes, as maintenance therapy to prevent re-initiation and relapse.

EXAMPLE 3

Clinical Treatment of Patient in Propagation Phase

A 25 year old female who just quit smoking, with a history of alcohol use, on birth pills, taking NSAIDS for aches and pains and laxatives for constipation, who lives on a high fat fast foods, with a demanding job and stressful personal life, and who has a cousin with ulcerative colitis is at high risk for induction and subsequent development of the disease. This patient presented with rectal bleeding which had been ongoing for about one year.

The patient was treated with a 150 cc rectal retention enema comprising sodium thiosulfate, bismuth subgallate, vitamin E, and cromolyn sodium administered once a day before bedtime for one month. After the first month, treatment was modified to administration of the enema every other day for an additional month. Dietary and lifestyle modification was also instituted. Rectal bleeding ceased by the third day of treatment and the patient has not exhibited any further rectal bleeding for about 8 months.

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES

Farrell, J. F., Peppercorn, M (2002) "Ulcerative colitis" *The Lancet* 359:331-340.

Blaut, M. (2000) "Assessment of bacteria in the gut microbial ecosystem" In: *Intestinal flora. European Concerted Action; Chapter 2*, page 1.

Basit, A., Bloor, J. (2003) "Perspective on Colonic Drug Delivery" In *Pharmatech* 2003, pp. 185-190, ed. Business Briefings Ltd., London.

Guyton, A., Hall, J. (1997) *Human physiology and mechanisms of disease*. Sixth Edition, Chapter 1, page 3, W. B Saunders 1997.

Brunner, L. S., Suddarth, D. S. (1980) Textbook of Medical Surgical Nursing ($4^{th}$ ed). Lippincott, Philadelphia, p. 358.

Benson, K. W., Bargen, J. (1939) Arnold. *Fecal Impaction Am. J. M. Sc.* 198:541-545.

Sheenan, J. F., Brynjolfsson, G. (1960) "Ulcerative colitis following hydrogen peroxide enema" *Lab Invest* 9:150-167.

Meyer, C. T. et al. (1981) "Hydrogen peroxide colitis: A report of three patients" *J Clin Gastroenetrol Mar;* 3(1): 31-5.

Bilotta, J. J., Waye, J. D. (1989) "Hydrogen peroxide enteritis: the "snow white" sign" *Gastrointest Endosc* September-October; 35(5):428-30.

Schwartz, E. et al. (1995) Letter to the editor *Dig. Dis. Sci.* June, 40(6): 1290-1.

Thibaud, D. et al. (2001) "Rectal bleeding: complication of hydrogen peroxide enemas" *Arch Pediatr.* 8(11):1267-8.

Chance, B., Sies, H., Boveris, A. (1979) "Hydroperoxide Metabolism in Mammalian Organs" *Physiological Reviews, Vol.* 59, No. 3.

Eaton, J. W., Qian, M. (2002) "Molecular basis of cellular Iron Toxicity" *Free Radicals in Biology and Medicine* 32(9):833-840.

Liu, S. S. (1997) "Generating, partitioning, targeting and functioning of superoxide in mitochondria" *Biosci. Rep.* 17:259-272.

Turrens, J. F. (1997) "Superoxide production by the mitochondrial respiratory chain" *Biosci. Rep.* 17:3-8.

Boveris, A, Chance, B. (1973) "The mitochondrial generation of hydrogen peroxide: General properties and effects of hyperbaric oxygen" *Biochem. J.* 134:707-716.

Reactive Oxygen Metabolites: CRC Press 2001 Manfred K. Eberhardt. pp. 51, 63, 64, 118, 125, 262.

Mitochondria in Pathogenesis. Kluwer Academic/Plenum Publishers. Lemasters J., Nieminen A. 2001, pp. 281-284, 286.

Han, D., Williams, E., Cadenas, E. (2001) "Mitochondrial respiratory chain-dependent generation of superoxide anion and its release into the intermembrane space" *Biochem. J.* 353:411-416.

Hoek J, et al. (2002) "Alcohol and mitochondria: A Dysfunctional Relationship" *Gastroenterology* 122: 2049-2063.

Boveris, A., Oshino, N., Chance, B. (1972) "The cellular production of hydrogen peroxide" *Biochem J.* 128:617-630.

Kehrer, James P. (2000) "The Haber-Weiss reaction and Mechanisms of Toxicity" *Toxicology* 149:43-50.

Fridovich, I. (1998) "Oxygen Toxicity: A Radical Explanation" *J. of Experimental Biology* 201:1203-1209.

Chen, S., Schopfer, P. (1999) "Hydroxyl radical production in physiological reactions" *Eur. J. Biochem* 260:726-735.

St.-Pierre, J. et. al. (2002) "Topology of superoxide production from Different Sites in the Mitochondrial Electron Transport Chain" *The Journal of Biological Chemistry* 277(47):44784-44790.

Boveris, A., Cadenas, E. (2000) *Life* 50:245-250.

Davies, J. A. Kelvin. (2000) *Life* 50:279-289.

Cadenas, E., Davies, J. A. Kelvin (2000) "Free Radicals in Biology and medicine" (29) 222-230.

Schultz, B. E., Chan, S. I. (2001) "Structures and Proton pumping Strategies of Mitochondrial Respiratory Enzymes" *Annu. Rev. Biophys. Biomol. Struct.* 30:23-65.

Eaton, J. W., Ma, M. (1995) Acatalasemia. *The Metabolic and Molecular Basis of Inherited Disease, 7$^{th}$ ed.*, pp. 2371-2379.

*The Metabolic and Molecular Basis of Inherited Disease.* (2001) 8$^{th}$ ed., p. 4650.

Meyers, S., Janowitz, H. D. (1989) "The "Natural History" of Ulcerative Colitis: An Analysis of the Placebo Response" *J. Clin. Gastroenetrol* 11(1):33-7.

National Guidelines Clearinghouse: http://www.ngc.gov "Management of Ulcerative Colitis" (comprehensive database of evidence-based clinical practice guidelines).

Blau, S. (1999) "Differences in the Reducing power along the rat GI tract: Lower antioxidant capacity of the colon" *Molecular and cellular Biochemistry* 194:185-91.

Matthew, B. et al. (1990) "Oxidant Defense Mechanisms in the Human Colon" *Inflammation* 14(6):669-80.

Roediger, W., Babige, W. (1997) "Human Colonocyte Detoxification" *Gut.* 41(6):731-34.

Owen, R W. et al. (2000) "Generation of Reactive Oxygen Species by the fecal Matrix" *Gut.* 46(2):225-32.

Harris, M. et al. (1992) "Free Radicals and other Reactive Oxygen Metabolites in Inflammatory Bowel Disease" *Pharmac Ther* 53:375-408.

Granger, D, Parks, D. (1983) "Role of Oxygen Radicals in the Pathogenesis of Intestinal Ischemia" *The Physiologist* 26(3):159-164.

Parks, D. et al. (1984) "Oxygen Radicals: Effects On Intestinal Vascular Permeability" *Gastrointest. Liver Physiol.* 10:G167-G170.

Parks, D, Granger, D. (1986) "Contributions of Ischemia and Reperfusion to Mucosal Lesion Formation" *Gastrointest. Liver Physiol.* 13:G749-G753.

Allison, M. C., Vallance, R. (1991) "Prevalence of Proximal Fecal Stasis in Active Ulcerative Colitis" *Gut.* 32(2):179-82.

Black, D. A. et al. (1987) "Transit Time in Ulcerative colitis" *Scand J. Gastroenterol.* 22:872-76.

Everson, C., Toth, L. (2000) "Systemic bacterial invasion induced by sleep deprivation" *Am. J. Physiolo Regulatory Integrative Comp Physiol.* 278:R905-R916.

Chuanyu, L., Jackson, R. (2002) "Reactive species mechanisms of cellular hypoxia-reoxygenation injury" *Am. J Physiol Cell Physiol.* 282; C227-C241.

Soderholm, J. et al. (2002) "Chronic Stress Induces Mast Cell-Dependant Adherence and Initiates Mucosal Inflammation in Rat Intestine" *Gastroenetrology* 123:1099-1108.

Soderholm, J., Perdue, M. (2001) "Stress and the Gastrointestinal Tract: Stress and intestinal Barrier Function" *Am J Gastrointest Liver Physiology* 280:G7-G13.

Lechin, F. et al. (1996) "Stress vs. Depression" *Prog. Neuro-Psychopharm. And Biol. Psychiat.* 20:899-950.

Cadenas, E., Davies, K. J. (2000) "Mitochondrial Free radical generation, oxidative stress and aging" *Free radic Biol Med.* 29(3-4):222-30.

Bertz, J., Granneman, G. R. (1997) "Use of In-Vitro and In-Vivi data to estimate the likelihood of Metabolic Pharacokinetic Interactions" *Clinical Pharmacokinetics* 32(3):210-58.

Hoek, J. et al. (2002) "Alcohol and mitochondria: A Dysfunctional Relationship" *Gastroenterology* 122:2049-2063.

Shannon, B. (1999) "Ethanol Stimulates The Production Of Reactive Oxygen Species At Mitochondrial Complexes I and III" *Free Radical Biology and Medicine* 27(7-8):891-900.

Hendrickson, B. A. "Clinical Aspects and Pathophysiology of Inflammatory Bowel Disease" *Clinical Microbiology Reviews* (2002), 15(1): 79-94.

Carpenter, H. A. (2000) "The importance of Clinicopathological Correlation in the Diagnosis of Inflammatory Conditions of the Colon: Histological Patterns With Clinical Implications", *American Journal of Gastroenterology* 95(4):878-893.

Shaw, A. et al (1967) "Gas Embolism produced By Hydrogen Peroxide", *The New England Journal of Medicine* 3; 277(5):238-41.

Pumphery R. E. (1951) "Hydrogen Peroxide Proctitis", *American Journal of Surgery* 81:60-62.

Drossman, D. et al. (2000) "ROME II. The Functional Gastrointestinal Disorders", *Diagnosis, Pathophysiology and Treatment. A Multinational Consensus,* 2nd ed., McLean Va. Degnan Associates.

Rao, S. (1988) "Symptoms and Stool Patterns in Patients with Ulcerative Colitis", *Gut* 29:342-245.

Drossman, D. et al. (1999) "U.S. Householder Survey of Functional Gastrointestinal Disorders: Prevalence, Sociodemography, and Health Impact" *Dig Dis Sci* 38:1569-80.

Everhart, J., et al. (1987) "A longitudinal survey of Self-Reported Bowel Habits in the United States", *Dig Dis Sci.* 32:841-5.

Topping L. and Clifton P. (2001) "Short Chain Fatty Acids and Human Colonic Function: Roles of Resistant Starch and Non Starch Polysaccharides" *Physiological Reviews* 82(3):1031-1064.

Roediger W. (1986) "Metabolic Induction of Experimental Ulcerative Colitis by Inhibition of fatty Acid Oxidation" Nance S. *Journal of Experimental Pathology* 67:773-782.

Gulati, S., et al. (1993) "Alterations of peroxisomal Function in ischemia-Reperfusion Injury of Rat Kidney" *Biochim Biophys Acta* 1182(3):291-98.

Bagchi, D. et al. (1998) "Stress, Diet and Alcohol-induced Gastrointestinal Mucosal Injury in Rats and Protection by BSS" *J Appl Toxicol.* 18(1):3-13.

Aw, T. (1999) "Molecular and Cellular Responses to Oxidative Stress and Changes in Oxidation-Reduction Imbalance in the Intestine" *American Journal of Clinical Nutrition* 70:557-65.

Maier, et al. (1974) "Effects of a High Beed Diet in Bowel Flora: A preliminary Report" *The Am. J. Of Clin. Nutrition* 27:1470-74.

Farrell, J. F., Peppercorn, M. (2002) "Ulcerative colitis" *The Lancet* 359:331-340

Reactive Oxygen Metabolites: CRC Press 2001 Manfred K. Eberhardt. pp. 23, 51, 63, 64, 81, 118, 125, 262.

Molloy, M. et al. (1999) "Increased Prevalence of Methylenetetrahydrofolate Reductase C677T Variant in Patients with Inflammatory Bowel Disease and its Clinical Implications" *Gut* 45(3):389-94.

Friedman, F. et al. (1999) "A Common Mutation A1298C in Human Methylenetetrahydrofolate Reductase Gene Association with Plasma Total Homocysteine and Folate Concentrations" *J. Nutr.* 129:1656-61.

Goyette, P. et al. (1999) "Gene Structure of Human and Mouse Methylenetetrahydrofolate Reductase" *Mammalian Genome* 9:652-656.

*The Metabolic and Molecular Basis of Inherited Disease*, Chapter 155, $8^{th}$ ed., Vol. 3, pp. 3897-3993.

Upchurch, et al. (1997) "Homocyst(e)ine Decreases Bioavailable Nitric Oxide by a Mechanism Involving Glutathione Peroxidase" *The Journal of Biological Chemistry* 272(27):17012-17017.

Wilcken, D. et al. (2000) "Relationship Between Homocysteine and Superoxide Dismutase in Homocysteinuria" *Aterioscler Thromb Vasc Biol.* 20:1199-1202.

Outinen, P. et al. (1999) "Homocysteine-Induced Endoplasmic Reticulum Stress and Growth Arrest Leads to Specific Changes in Gene Expression in Human Vascular Endothelial Cells" *Blood* 94(3):959-967.

Chen, N. (2000) "Physiologic Concentrations of Homocysteine Inhibit the Human plasma GSH peroxidase that Reduces Organic Hydroperoxides" 136(1):58-65.

Whelan, G. (1990) "Epidemeology of Inflammatory Bowel Disease" *Med Ckin North Am.* 74(1):1-12.

Farrokhar, F. et al. (2001) "A Critical Review of Epidemiological Studies in Inflammatory Bowel Disease" *Scand J. Gastroenterology* 36(1):2-15.

Rady, P. L. et al. (1999) "Methylenetetrahydrofolate Reductase (MTHFR): The Incidence of Mutations C677T and A1298C in the Ashkenenazi Jewish Population" *Am. J. Med Genet.* 86(4):380-4.

Roth, M. P. et al. (1989) "Geographic Origins of Jewish Patients With Inflammatory Bowel disease" *Gastroenterology* 97(4):900-4.

Karlinger, K. (2000) "The Epidemiology and the Pathogenesis of Inflammatory Bowel Disease" *Eur. J Radiol.* 35(3):154-67.

Fernandez-Banares, F. et al. (1989) "Vitamin Ststus in Patients with Inflammatory Bowel Disease" *Am. J. Gastroenterol.* 84(7):744:8.

Elsborg, L., Larsen, L. (1979) "Folate deficiency in Chronic Inflammatory Disease" *Scand J. Gastroenterology* 14(8): 1019-24.

Koutroubakis, I. E. (2000) "Hyperhomocysteinemia in Greek Patients with Inflammatory Bowel Disease" *Dig Dis Sci.* 45(12):2347-51.

Duncan, G. (1964) Disease of Metabolism, $5^{th}$ ed., p. 617.

Geerling, B. J. et al. (2000) "Diet as a Risk factor For the Development of Ulcerative Colitis" *Am J Gastroenetrology* 95(4): 1008-13.

Keyer, K., Imlay J. (1996) "Superoxide accelerates DNA damage by elevating free iron levels" *Proc. Nat'l Acad. Sci.* 93:13635-640.

Liochev S., Fridovich I. (1999) "Superoxide and Iron: Partners in Crime" *IUBMB Life* 48:157-161.

Srigiridhar, K. et al. (2001) "Oral Repletion of Iron Induces Free Radical Medicated Alterations in the Gastrointestinal Tract of Rat" *Mol Cell Biochem.* 219(1-2):91-98.

Reifen, R. et al. (2000) "Iron Supplementation May Aggravate Inflammatory Status of Colitis in Rat Model" *Dig Dis Sci.* 45(2):394-7.

Graf, E. et al. (1984) "Iron Catalyzed Hydroxyk Radical Formation" *The Journal of Biological Chemistry* 259(6): 3620-3624.

Millar, A. D. et al. (2000) "Effects of Iron and Iron Chelation In Vitro on Mucosal Oxidant Activity in Ulcerative Colitis" *Aliment Pharmacol Ther.* 14(9):1163-8.

Kawai, M. et al. (1992) "A Case of Ulcerative Colitis Induced By Oral ferrous Sulfate" *Acta Paediatr Jpn.* 34(4):476-8.

Dalekos, G. N. et al. (1998) "Zinc, Copper and Immunological Markers in the Circulation of Well Nourished Patients With Ulcerative Colitis" *Eur J. Gastroenterol Hepatol.* 10(4): 331-7.

Ringstad, J. et al. (1993) "Serum Selenim, Copper and Zinc concentrations in Crohn's Disease and Ulcerative Colitis" 28(7):605-8.

Torisu, T. et al. (2002) "A rare case of Ulcerative Colitis Complication Wilsons's Disease: possible association between the two diseases" *J Clin Gastroenetrol.* 35(1): 43-5.

Madretsma, S. (1996) "In-vivo Effect of Nicotine on Cytokine Production by Human Non-adherent Mononuclear Cells" *Eur J. Gastroenterol Hepatol.* 8(10):1017-20.

Abrham, N. et al. (2003) "Is Smoking an Indirect Risk Factor for the Development of Ulcerative Colitis? An age- and Sex-Matched case-Control Study" *Eur J. Gastroenterol Hepatol.* 18(2): 139-46.

Odes, H. S. (2001) "Effects of Current Cigarette Smoking on Clinical Course of Crohn's Disease and Ulcerative Colitis" *Dig Dis Sci.* 46(8): 1717-21.

Pryor, W. et al. (1992) "The Inhibitory Effect of Extracts of Cigarette Tar On Electron Transport Of Mitochondria And Submitochondrial Particles" *Free Radicals in Biology and Medicine* 12:365-372.

Ouyang, Y. et al. (2000) "Suppression of Human IL-1 beta, IL-2, IFN gamma, and TNF-alpha Production by Cigarette Smoke and Extracts" *J Allergy Clin Immunology* 106(2):280-7.

Fowler, J. S. et al. (2003) "Monoamine Oxidase and Cigarette Smoking" *Neurotoxicology* 24(1):75-82.

Van Fleet, T. R. et al. (2001) "Inhibition of Human Cytochrome P450 2E1 by Nicotine, Cotinine and aqueous Cigarette Tar Extract In-vitro" *Toxicol Sci.* 64(2): 185-91.

Beaugerie. L. et al. (2001) "Impact of Cessation of Smoking on the Course of Ulcerative Colitis" *Am J Gastroenterol.* 96(7):2113-6.

Clearing the Smoke: Assessing the Science Base for Tobacco Harm Reduction. The National Academy of Sciences. 2001. Chap. 9 p. 267, http://www.nap.edu/openbook/0309072824/html/index.html.

Modebe, O. (1986) "Autoimmune Thyroid Disease With Ulcerative Colitis" *Postgraduate Medical Journal* 62:475-476.

Jarnerot, G. et al. (1975) "The Thyroid In Ulcerative Colitis and Crohn's Disease" *Acta Med. Scand.* 197:83-87.

Venditti, P. et al. (2003) "Effects of Thyroid State on $H_2O_2$ production by Rat heart Mitochondria" *Hormone Metabolic Research* 35:55-61.

Goglia, F. et al. (2002) "Thyroid Hormones and Mitochondria" *Bioscience Reports* 22(1):17-32.

Venditti, P. et al. (1997) "Effect of Thyroid State on Lipid Peroxidation, Antioxidant defenses, and Susceptibility to Oxidative Stress in Rat Tissues" *Journal of Endocrinology* 155:151-157.

Isman et al. (2003) "Methimazole-Induced Hypothyroidism in Rats Ameliorates Oxidative Injury in Experimental Colitis" *Journal of Endocrinology* 177:471-476.

Maaravi, O. et al. (1997) "Anti-thyroid Drugs Decreases Mucosal Damage in a Rat Model of Experimental Colitis" *Alimint. Pharmacol. Ther.* 11(2):341-5.

Cho et al. (2000) "Linkage and Linkage Disequilibrium in Chromosome band 1p36 in American Chaldeans With Inflammatory Bowel Disease" *Human Molecular Genetics* 9(9):1425-1432.

Cho et al. (1988) "Identification of Novel Susceptibility Loci For Inflammatory Bowel Disease on Chromosomes 1p, 3q and 4q" *Proc. Natl. Acad. Sci.* 95:7502-07.

Davidson, R. (1967) "Electrophoretic Variants of Human 6-phosphogluconate dehydrogenase: Population Study and Family Studies and Description of a New Variant" *Ann. Hum. Genet.* 30:355-361.

Parr, C. W. (1966) "Erythrocyte Phosphogluconate Dehydrogenase Polymorphism" *Nature* 210:487-489.

Parr, C. W. (1967) "Inhereted Quantitative Variations of Human Phosphogluconate Dehydrogenase" *Ann. Hum. Genet.* 30:339-53.

Dern, J. et al. (1966) "Hereditary Variation of Erythrocytic 6-phosphogluconate dehydrogenase" *J. lab & Clin Med.* 67(2) "255-64.

Nelson, M. S. (1982) "Biochemical and Genetic Characterization of the Lowell Variant. New Phenotype of 6-phosphogluconate Dehydrogenase" 62:333-336.

Capari, P. (2001) "6-Phosphogloconate Dehydrogenase deficiency in an Italian Family" *Ann hematol* 80:41-44.

Cifci, M. (2002) "Effects of Some Drugs on Rat Erythrocyte 5-Phosphogluconate Dehydrogenase" *Pol. J. Pharmacol.* 54(3):275-80.

Tomlinson, J. E. (1998) "Repression of Pentose Phosphate Pathway Dehydrogenase Synthesis and mRNA by Dietary Fat in Rats" 118(3):408-15.

Gordillo, E. (1991) "Implication of Lysine Residues in the Loss of 6-Phosphogluconate Dehydrogenase in Aging Human Erythrocytes" *Mech Ageing Dev.* 59(3):291-7.

Batist, G. et al. (1998) "Interindividual Variation in Phase II Detoxification Enzymes in Normal Colon Mucosa" *Biochemical Pharmacology* 37(21):4241-4243.

Scriver C. R. et al. Editors. *The Metabolic and Molecular Basis of Inherited Disease.* 8$^{th}$ edition 2001, pp. 4650-4651.

Larsson, A., Anderson, M. (2001) "Glutathione Synthetase Deficiency and Other Disorders of the gamma-Glutamyl Cycle" In *The Metabolic and Molecular Basis of Inherited Disease.* 8$^{th}$ edition, pp. 2205-2215.

Buetler, E., Matsumoto, F. (1975) "Ethnic Variation in Red Cell Glutathione Peroxidase activity" *Blood* 46(1):103-110.

O'Donnell, V., Azzi, A. (1996) "High Rates of Extracellular Superoxide Generation by Cultured Human Fibroglasts" *Biochem Journal* 318:805-812.

Souchard, J. P. et al. (1998) "Electron Spin Resonance Detection of Extracellular Superoxide Anion Released by Cultured Endothelial Cells" *Free Radical Research* 29(5):441-449.

Huycke, M. M. et al. (2002) "Enterococcus Faecalis Produces Extracellular Superoxide and Hydrogen Peroxide That Damages Colonic Epithelial DNA" *Carcinogenesis* 3:529-536.

Huycke, M. M., Moore, D. R. (2002) "In Vivo Production of Hydroxyl Radical by Enterococcus Faecalis Colonizing the Intestinal Tract Using Aromatic Hydroxylation" *Free Radicals in Biology and Medicine* 33(6):818-826.

Huycke, M. M. et al. (2001) "Extracellular Superoxide Production by Enterococcus Faecalis Requires Demethylmenaquinone and is Attenuated by Functional Terminal Quinol Oxidases" *Molecular Microbiology* 42(3):729-740.

I claim:

1. A composition for the treatment of inflammatory bowel disorders selected from the group consisting of ulcerative colitis, Crohn's disease and irritable bowel disorder comprising a reducing agent and an NADPH-oxidase inhibitor, wherein said reducing agent is sodium thiosulfate and said composition further comprises bismuth subgallate, vitamin E, and sodium cromolyn.

2. The composition according to claim 1, wherein said NADPH-oxidase inhibitor is DMSO, apocynin, or trental (pentoxifylline).

3. The composition according to claim 1, wherein said sodium thiosulfate and said NADPH-oxidase inhibitor is apocynin.

4. The composition according to claim 3, wherein said composition is provided in a dosage form suitable for rectal administration or in a form suitable for oral administration, wherein said oral dosage from exhibits the characteristic of delayed dissolution until said oral dosage form is present in the colon of an animal.

5. The composition according to claim 1, wherein said composition is provided in purified form.

6. A pharmaceutical composition comprising a composition as defined in claim 1 and a pharmaceutically-acceptable carrier.

7. A pharmaceutical composition comprising according to claim 6, wherein said composition comprises sodium thiosulfate and apocynin.

8. A pharmaceutical composition comprising according to claim 6, wherein said pharmaceutical composition is provided in a dosage form suitable for rectal administration or in a form suitable for oral administration, wherein said oral dosage form exhibits the characteristic of delayed dissolution until said dosage form is present in the colon of an animal.

* * * * *

UNITED STATES PATENT AND TRADEMARK OFFICE
CERTIFICATE OF CORRECTION

PATENT NO. : 7,312,243 B1
APPLICATION NO. : 10/927742
DATED : December 25, 2007
INVENTOR(S) : Jay Pravda It is certified that error appears in the above-identified patent and that said Letters Patent is hereby corrected as shown below:

Column 36
Lines 41-42, "wherein said sodium thiosulfate and said NADPH-oxidase" should read --wherein said NADPH-oxidase--

Line 47, "dosage from exhibits" should read --dosage form exhibits--

Line 55, "a pharmaceutical composition comprising according" should read --The pharmaceutical composition according--

Line 58, "a pharmaceutical composition comprising according" should read --The pharmaceutical composition according--

Line 63, "until said dosage" should read --until said oral dosage--

Signed and Sealed this

Eighteenth Day of August, 2009

David J. Kappos
*Director of the United States Patent and Trademark Office*